United States Patent
Jacob et al.

(10) Patent No.: US 11,660,270 B2
(45) Date of Patent: May 30, 2023

(54) NANOPARTICLE COMPOSITIONS

(71) Applicants: Indiana University Research and Technology Corporation, Indianapolis, IN (US); Yissum Research Development Company of the Hebrew University of Jerusalem Ltd., Jerusalem (IL)

(72) Inventors: Domb Abraham Jacob, Jerusalem (IL); Michael Kubek, Indianapolis, IN (US)

(73) Assignees: INDIANA UNIVERSITY RESEARCH AND TECHNOLOGY CORPORATION, Indianapolis, IN (US); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/632,759

(22) PCT Filed: Jul. 20, 2018

(86) PCT No.: PCT/IL2018/050807
§ 371 (c)(1),
(2) Date: Jan. 21, 2020

(87) PCT Pub. No.: WO2019/016819
PCT Pub. Date: Jan. 24, 2019

(65) Prior Publication Data
US 2020/0323777 A1    Oct. 15, 2020

Related U.S. Application Data

(60) Provisional application No. 62/534,787, filed on Jul. 20, 2017, provisional application No. 62/534,818, filed on Jul. 20, 2017.

(51) Int. Cl.
*A61K 9/14* (2006.01)
*A61K 9/51* (2006.01)
*A61K 9/00* (2006.01)
*A61K 45/06* (2006.01)

(52) U.S. Cl.
CPC ............ *A61K 9/145* (2013.01); *A61K 9/5153* (2013.01); *A61K 9/5192* (2013.01); *A61K 9/0043* (2013.01); *A61K 45/06* (2013.01)

(58) Field of Classification Search
CPC .... A61K 9/145; A61K 9/5153; A61K 9/5192; A61K 9/0043; A61K 45/06; A61K 31/436; A61K 31/05; A61K 38/095; A61K 9/5146; A61K 38/066; A61K 38/00; A61K 38/13; A61K 31/352
See application file for complete search history.

(56) References Cited

U.S. PATENT DOCUMENTS

| | | | | |
|---|---|---|---|---|
| 5,611,971 A | * | 3/1997 | Maedera | A61K 9/1694 264/4.1 |
| 2003/0211966 A1 | * | 11/2003 | Kubek | A61K 9/0085 424/434 |
| 2007/0154559 A1 | | 7/2007 | Pai et al. | |
| 2008/0190424 A1 | * | 8/2008 | Lucking | A61M 15/0008 128/203.15 |
| 2013/0042864 A1 | * | 2/2013 | Adler | A61M 15/0008 128/203.15 |

OTHER PUBLICATIONS

Hiremath Paclitaxel polySA-RA nanoparticles Asian J. Pharma, p. 225 (Year: 2011).*
Kubek (a) Intranasal Delivery Neuropeptide, Adv. Delivery Sci. Tech, p. 195, (Year: 2014).*
Kubek (b) implantable TRH microdisk prep. Brain Res. p. 189, 1998 (Year: 1998).*
Tabata Inj. Polyanhydride Granules Controlled Release of Drugs, J. Pharm. Sci. p. 5 (Year: 1994).*
Bagherifam PSA nanocapsules, J. Microencapsul., p. 166 (Year: Oct. 2014).*
Yamasaki, Enhanced dissolution with mannitol, Intl. J. Pharmaceutics, p. 34 (Year: Aug. 2011).*
Vedula, Preparation of nanoparticles, Appl Nanosci. 6, p. 197, (Year: Feb. 2015).*
Afra et al., "The influence of mannitol on morphology and disintegration of spray-dried nano-embedded microparticles", European Journal of Pharmaceutical Sciences, vol. 104, Apr. 5, 2017, pp. 171-179.
Hiremath et al., "Paclitaxel loaded poly(sebacic acid-coricinoleic ester anhydride)-based nanoparticles", Asian Journal of Pharmaceutics, vol. 5, No. 4, 2011, 225 pages.
Huertas et al., "Polymer-based nanocapsules for drug delivery", International Journal of Pharmaceutics, vol. 385, No. 1-2, Jan. 29, 2010, pp. 113-142.
Ivana et al., "Overcoming barriers inPseudomonas cationic antimicrobial peptide", Colloids and Surfaces, vol. 135, Aug. 22, 2015, pp. 717-725.

(Continued)

*Primary Examiner* — Matthew P Coughlin
*Assistant Examiner* — Thurman Wheeler
(74) *Attorney, Agent, or Firm* — Faegre Drinker Biddle & Reath LLP

(57) ABSTRACT

Compositions comprising nanoparticles are described herein. At least a portion of the nanoparticles comprises a lipid and/or polymer which is water-insoluble, and an agent incorporated in the lipid and/or polymer. The nanoparticles are optionally associated with a surface of water-soluble particles which comprise a water-soluble compound. The polymer is optionally a polyanhydride. Further described herein are processes for preparing such compositions, comprising contacting a solution comprising the lipid and/or polymer dissolved in a non-aqueous solvent with an antisolvent (in which the lipid and/or polymer and agent are insoluble) which is miscible with the non-aqueous solvent. Further described herein are uses of the compositions for nasal administration, and devices configured for nasal administration of the composition upon atomization.

**16

(56) References Cited

OTHER PUBLICATIONS

Kubek et al., "Intranasal Delivery of Neuropeptide-Loaded Nanoparticles and Their Application to Nervous System Therapeutics", In: "Advances in Delivery Science and Technology", 2014, XP055515442.

Peltonen et al., "Improved entrapment efficiency of hydrophilic drug substance during nanoprecipitation of poly(I)lactide nanoparticles", AAPS PharmSciTech, Mar. 8, 2004, p. E16, XP055515673.

* cited by examiner

NANOPARTICLE COMPOSITIONS

CROSS-REFERENCE TO RELATED APPLICATIONS

This application is the U.S. National Stage Application of International Patent Application No. PCT/IL2018/050807, filed Jul. 20, 2018, which claims priority to and the benefit of U.S. Provisional Application No. 62/534,787, filed Jul. 20, 2017 and U.S. Provisional Application No. 62/534,818, filed Jul. 20, 2017, the disclosures each of which is incorporated herein by reference in its entirety.

STATEMENT OF GOVERNMENT SUPPORT

This invention was made with government support under W81XWH-12-1-0005 awarded by U.S. Army Medical Research & Material Command (MRMC). The government has certain rights in the invention.

FIELD AND BACKGROUND OF THE INVENTION

The present invention, in some embodiments thereof, relates to delivery systems, and more particularly, but not exclusively, to lipid and/or polymeric nanoparticles usable for incorporating therein, and delivering, agents such as therapeutically active agents (drugs), such as therapeutic peptides, and to formulations containing these nanoparticles.

Over the past few decades, much effort has been devoted to developing nanotechnology for drug delivery because of its suitability and feasibility in delivering small molecular weight drugs, as well as macromolecules such as proteins, peptides or genes by either localized or targeted delivery to the tissue or cell of interest.

Drug-loaded solid lipid or polymeric nanoparticles are typically prepared from biodegradable polymers or fatty acid based materials, which degrade chemically under physiological conditions and do not require removal after placed in the body. For most applications, polymers and lipids should be non-toxic, biocompatible and biodegradable.

In general, diffusion of the drug and biodegradation of the carrier material control the drug release from biodegradable nanoparticles. Several factors can contribute to the release rate of encapsulated or surface-adsorbed drugs from nanoparticles. These include desorption of the surface-bound or adsorbed drug, diffusion of the drug through the matrix structure or the polymeric membrane, erosion of the matrix or a combined erosion and diffusion process.

There are several different methods available for the preparation of polymeric nanoparticles, and these methods can be roughly divided into two main categories [Pinto Reis et al., *Nanomedicine* 2006, 2:8-21]. The preparation method is usually selected based on the properties the carrier material and the drug molecule to be encapsulated.

Polymer nanoparticles can be conveniently prepared either from preformed polymers or by direct polymerization of monomers using classical polymerization or polyreactions. Methods such as solvent evaporation, salting-out, dialysis and supercritical fluid technology, involving the rapid expansion of a supercritical solution or rapid expansion of a supercritical solution into liquid solvent, can be utilized for the preparation of polymer nanoparticles from preformed polymers. On the other hand, polymer nanoparticles can be directly synthesized by the polymerization of monomers using various polymerization techniques such as micro-emulsion, mini-emulsion, surfactant-free emulsion and interfacial polymerization.

One of the most widely used methods for polymeric nanoparticles preparation is the nanoprecipitation method (solvent displacement). The basic principle of this technique is believed to be based on the interfacial deposition of a polymer after displacement of a semipolar solvent, miscible with water, from a lipophilic solution. Rapid diffusion of the solvent into non-solvent phase results in the decrease of interfacial tension between the two phases, which increases the surface area and leads to the formation of small droplets of organic solvent [Mishra et al., *Nanomedicine* 2010, 6:9-24].

Nanoprecipitation system consists of three basic components: the polymer, the polymer solvent, and the anti-solvent of the polymer (typically an aqueous medium). A surfactant may also be used, although it is not directly involved in the formation of nanoparticles. Instead, its function is to maintain steric stability of the formed nanoparticles.

The nanoprecipitation technique is typically useful only for preparing hydrophobic drug-based nanoparticles, as entrapment efficiency of hydrophilic drugs is typically very low [Saallah & Lenggoro, *KONA Powder Particle J* 2018, 35:89-111; C. Vauthier, G. Ponchel (Eds.), *Polymer Nanoparticles for Nanomedicines*, Springer International Publishing, Switzerland, 2016]. Emulsion techniques are considered practical when nanoparticles of water soluble drugs are prepared [Vila et al., *J Control Release* 2002, 78:15-24; El-Say & El-Sawy, *Int J Pharm* 2017, 528:675-691].

Govender et al. [*J Control Release* 1999, 57:171-185] describes the poor incorporation of water-soluble drugs in nanoparticles prepared by nanoprecipitation, and reports that incorporation efficiency of procaine (a hydrophilic drug) in PLGA (poly(di-lactide-co-glycolide)) nanoparticles could be enhanced by modifying the pH and including PMMA-MA (poly(methyl methacrylate-co-methacrylic acid)), lauric acid and caprylic acid.

Peltonen et al. [*AAPS PharmSciTech* 2004, 5:E16] reports that entrapment of hydrophilic sodium cromoglycate in polylactic acid nanoparticles prepared by nanoprecipitation was enhanced by lowering the pH of the aqueous medium.

Bilensoy et al. [*Int J Pharm* 2009, 371:170-176] reports encapsulation of mitomycin C in cationic nanoparticles of chitosan, or polycaprolactone coated with chitosan or polylysine, for delivery to bladder tumors.

Bilati et al. [*AAPS PharmSciTech* 2005, 6:E594-E604] reports successful use of nanoprecipitation to encapsulate of proteins such as insulin and lysozyme in polylactic acid and PLGA nanoparticles, by using miscible organic solvents such as DMSO and ethanol instead of the common acetone and water.

Yoo et al. [*J Pharm Sci* 2001, 90:194-201] reports formation of PLGA nanoparticles with lysozyme or lysozyme-oleate complex, by dissolving the lysozyme in DMSO, and slowly adding the DMSO solution to an aqueous poloxamer 407 solution.

Yamasaki et al. [*Int Journal Pharm* 2011, 420:34-42] describes inhalable cyclosporine nanoparticles with mannitol used to form a hydrophilic nano-matrix. Mannitol was dissolved in cyclosporine nano-suspensions, followed by spray drying to obtain micron-sized aggregates.

The nano-suspensions were prepared by mixing an ethanolic solution of the drug with water.

Polyanhydrides such as polysebacic acid have been shown to be suitable for use in vivo, undergoing hydrolysis to their constituent diacids [Leong et al., *J Biomed Mater*

1986, 20:51-64; Domb & Nudelman, *Biomaterials* 1995, 16:319-323; Domb et al., *Biomaterials* 1994, 15:681-688].

U.S. Patent Application Publication No. 2015/0216888 describes polyanhydride nanoparticles loaded with antiparasitic agents, as well as nanoparticle synthesis by adding a solution of polyanhydride in dichloromethane to a petroleum ether or pentane anti-solvent. U.S. Pat. Nos. 88,927,024 and 8,449,916 describe similar polyanhydride nanoparticles with antimicrobialagents.

Thyrotropin-releasing hormone (TRH), a hypothalamic neurohormone having the sequence pyroglutamyl-histidyl-proline-amide (pyro-Glu-His-Pro-$NH_2$) has been reported to be effective in treating depression, epilepsy, brain injury, acute spinal trauma and schizophrenia [Jackson, *N Engl J Med* 1982, 306:145-155; Metcalf, *Brain Res Rev* 1982, 4:389-408; Griffiths, *Clin Sci* 1987, 73:449-457; Horita et al., *Annu Rev Pharmacol Toxicol* 1986, 26:311-332; Loosen, *Progr Neuro-Psychopharmacol Biol Psychiatr* 1988, 12:S87-S117].

However, the entry of TRH into brain is limited due to its hydrophilic nature, large size and rapid metabolism, as these properties make it unsuitable for passage through blood brain barrier (BBB). TRH is rapidly metabolized in the stomach, liver, and kidney [Bauer, *Biochimie* 1988, 70:69-74; Wilk, *Ann N.Y. Acad Sci* 1989, 553:262-264; Bauer, *Trends Endocrinol Metabol* 1995, 6:101-105], and has a plasma half-life of only about 8 minutes, primarily due to rapid enzymatic degradation of the peptide in the blood by serum pyroglutamyl aminopeptidase [Duntas et al., *Klinische Wochenschrift* 1990, 68:1013-1019; Bassiri & Utiger, *J Clin Invest* 1973, 52:1616-1619; Iversen, *J Endocrinol* 1988, 118:511-516]. Attempts to address these deficiencies include the preparation of lipophilic and other analogs of TRH, but many of these analogs are unsatisfactory, for example, not as therapeutically effective as TRH. In addition, large amounts of TRH may be administered in order to overcome the obstacles to TRH administration, but this can lead to enhanced side effects, such as flushing, nausea and transient increase in blood pressure, due to the initial high plasma concentrations of the drug.

The nasal cavity provides a possible alternative route for administration of drugs to the central nervous system. Uptake and transport of drugs by the olfactory and/or trigeminal nerves can bypass the BBB. In order to be suitable for nasal delivery, a drug should fulfill certain requirements [Chien, in *Novel Drug Delivery Systems*, J. Swarbrick (Ed.), pp. 139-196, New York: Marcel Dekker, 1992], such as a pKa which is close to the pH of the nose (pH~5.5-6.5), a low molecular weight and size, and mucoadhesive properties. The drug concentration and volume should be low, such that the dispersion of the drug is uniform and effective [Illum, *J Pharm Sci* 2007, 96:473-483; Appasaheb et al., *J Adv Pharm Edu Res* 2013, 3:333-346; Constantino et al., *Int J Pharm* 2007, 337:1-24].

Although TRH fulfills some of the requirements of nasal delivery, adsorption of the charged hydrophilic TRH peptide on the mucosal layer and entrance through the nasal epithelium represents a serious obstacle to nasal delivery [Ibraheem et al., *Int J Pharm* 2014, 477:578-589]. The use of TRH in nanoparticles has been considered to overcome the obstacles to nasal delivery of TRH per se.

Direct nose-to-brain drug delivery using nanoparticles has been demonstrated in animal models [Mistry et al., *Int J Pharm* 2009, 379:146-157].

Kubek et al. [*Neurotherapeutics* 2009, 6:359-371] reports that intranasal administration of polylactide nanoparticles containing TRH can impede convulsive activity in an animal model of epilepsy.

Kubek et al. [in Focal Controlled Drug Delivery, A. J. Domb & W. Khan (Eds.), pp. 195-213, Controlled Release Society, 2014] describes TRH-loaded polylactide (PLA) and poly(lactide-co-glycolide) (PLGA) nanoparticles as releasing the TRH mostly as an initial burst, with the polymer capsule degrading at a much slower rate, which may lead to toxic polymer buildup in the brain upon repeated administration. It is proposed that TRH-loaded polyanhydride nanoparticles would release TRH for nose-to-brain delivery at a controlled rate upon polymer hydrolysis, although such nanoparticles are more complex to synthesize and load.

Burst release harms treatment efficacy, as the drug is lost in an uncontrolled and unpredictable pattern [Brazel & Huang, *ACS Symposium Series*, Ch. 1 2004, 879:267-282; Kamaly et al., *Chem Rev* 2016, 116:2602-2663].

Additional background art includes Anders & Merkle [*J Pharm Sci* 1983, 72:1481-1483]; Bilati et al. [*Eur J Pharm Sci* 2005, 24:67-75]; Burnette & Marre [*J Pharm Sci* 1986, 75:738-743]; Chiamolera & Wondisford [*Endocrinology* 2009, 150:1091-1096]; Chiou et al [*Aerosol Sci* 2008, 39:500-509]; Domb & Langer [*J Polym Sci A Polym Chem* 1987, 25:3373-3386]; Gozes et al. [*Proc Nat Acad Sci USA* 1996, 93:427-432]; Grant et al. [*Biochemistry* 1972, 11:3070-3073]; Han et al. [*Polymers* 2018, 10:31-45]; Joseph-Bravo et al. [*J Endocrinol* 2015, 226:&85-T100]; Kubek et al. [*Brain Res* 1998, 809:189-197]; Kumar & Langer [*Adv Drug Deliv Rev* 2002, 54:889-910]; Lehrer [*J Clin Psychopharmacol* 2014, 34:288-290]; Leong et al. [*Macromolecules* 1987, 20:705-712]; Mathiowitz et al. [*Nature* 1997, 386:410-414]; Mittal et al. [*Drug Deliv* 2014, 21:75-86]; Msss & Bundgaard [*Int J Pharm* 1990, 66:39-45]; Nillni [*Front Neuroendocrinol* 2010, 31:134-156]; Sabir et al. [*J Mater Sci* 2009, 44:5713-5724]; Schifgen et al. [*Horm Metab Res* 1983, 15:52-53]; Schurr et al. [*J Endocrinol Invest* 1985, 8:41-44]; Suchowersky et al. [*Movement Disorders* 1995, 10:337-340]; Vauthier et al. [*Eur J Pharm Biopharm* 2008, 69:466-475]; Vedula et al. [*Appl Nanosci* 2016, 6:197-208]; Xu et al. [*Polym Bull* 2001, 46:435-442]; and Zhang et al. [*J Nanomater* 2010, Article ID 898910, 1-5].

SUMMARY OF THE INVENTION

According to an aspect of some embodiments of the invention, there is provided a composition comprising a plurality of nanoparticles, at least a portion of the nanoparticles are nanoparticles comprising a lipid and/or polymer, the lipid and/or polymer being water-insoluble, and an agent incorporated in the lipid and/or polymer, wherein the nanoparticles are associated with a surface of water-soluble particles which comprise at least one water-soluble compound.

According to an aspect of some embodiments of the invention, there is provided a process for preparing a composition described herein, the process comprising contacting a solution comprising the lipid and/or polymer described herein dissolved in a non-aqueous solvent with a dispersion of the water-soluble particles described herein in an anti-solvent, wherein the anti-solvent is miscible with the non-aqueous solvent and wherein the lipid and/or polymer, the agent and the water-soluble compound described herein are each insoluble in the anti-solvent.

According to an aspect of some embodiments of the invention, there is provided a process for preparing nanoparticles comprising a polyanhydride and an agent incorporated in the polyanhydride, the process comprising contacting an anhydrous solution comprising the agent and the polyanhydride dissolved in a solvent with an anhydrous anti-solvent, wherein the anti-solvent is miscible with the solvent and the agent and the polyanhydride are each insoluble in the anti-solvent.

According to an aspect of some embodiments of the invention, there is provided a composition comprising nanoparticles prepared according to a process described herein.

According to an aspect of some embodiments of the invention, there is provided a composition comprising nanoparticles, the nanoparticles comprising a polyanhydride, and a therapeutically active agent incorporated in the polyanhydride, the composition being for use in treating a condition in which administration of the therapeutically active agent is beneficial, wherein the treating comprises nasal administration of the composition.

According to an aspect of some embodiments of the invention, there is provided a device comprising a composition described herein, the device being configured for atomization of the composition and nasal administration of the composition upon atomization.

According to some of any of the embodiments described herein, the composition comprises water-soluble particles which comprise at least one water-soluble compound, wherein the nanoparticles are associated with a surface of the water-soluble particles.

According to some of any of the embodiments described herein relating to water-soluble particles, the at least one water-soluble compound is selected from the group consisting of a saccharide, an alcohol, a salt and a water-soluble polymer.

According to some of any of the embodiments described herein relating to water-soluble particles, the at least one water-soluble compound comprises a sugar alcohol.

According to some of any of the embodiments described herein, upon contact with water, the nanoparticles disperse within no more than two minutes.

According to some of any of the embodiments described herein, the lipid and/or polymer is a biodegradable solid.

According to some of any of the embodiments described herein relating to a lipid in the nanoparticles, the lipid is selected from the group consisting of a triglyceride, a fatty acid, a fatty alcohol, and a fatty acid ester.

According to some of any of the embodiments described herein relating to a polymer in the nanoparticles, the polymer is selected from the group consisting of a polyanhydride, a polyester, a polyether, and copolymers thereof.

According to some of any of the embodiments described herein, the polymer is a polyanhydride.

According to some of any of the embodiments described herein, the polymer is selected from the group consisting of poly(1,3-bis-carboxyphenoxypropane-co-sebacic acid) (P(CPP:SA)) and polysebacic acid (PSA).

According to some of any of the embodiments described herein, the polymer is polysebacic acid and the at least one water-soluble compound comprises mannitol.

According to some of any of the embodiments described herein, an average diameter of the nanoparticles comprising a lipid and/or polymer is in a range of from 10 nm to 1000 nm.

According to some of any of the embodiments described herein, an average diameter of the nanoparticles comprising a lipid and/or polymer is in a range of from 200 nm to 600 nm.

According to some of any of the embodiments described herein, an average diameter of the water-soluble particles is in a range of from 500 nm to 50000 nm.

According to some of any of the embodiments described herein, a weight ratio of the nanoparticles comprising a lipid and/or polymer to the water-soluble particles is in a range of from 1:2 to 1:100.

According to some of any of the embodiments described herein, a concentration of the agent in the nanoparticles comprising a lipid and/or polymer is at least 5 weight percents.

According to some of any of the embodiments described herein, the agent is water-soluble.

According to some of any of the embodiments described herein, the agent is a therapeutically active agent.

According to some of any of the embodiments described herein, a concentration of a therapeutically active agent in the nanoparticles comprising a lipid and/or polymer is at least 5 weight percents.

According to some of any of the respective embodiments described herein, the therapeutically active agent is water-soluble.

According to some of any of the respective embodiments described herein, the therapeutically active agent is a peptide or polypeptide.

According to some of any of the respective embodiments described herein, the therapeutically active agent is selected from the group consisting of thyrotropin-releasing hormone (TRH), gonadotropin-releasing hormone (LHRH), oxytocin, insulin, corticotropin (ACTH), cyclosporin, steroids, cannabidiol (CBD), tetrahydrocannabinol (THC), rapamycin, and antibiotics.

According to some of any of the embodiments described herein, the nanoparticles comprise thyrotropin-releasing hormone and polysebacic acid.

According to some of any of the embodiments described herein, the nanoparticles comprise a lipid and/or polymer comprise thyrotropin-releasing hormone and polysebacic acid, and the at least one water-soluble compound comprises mannitol.

According to some of any of the embodiments described herein relating to a composition comprising a therapeutically active agent, the composition is for use in treating a condition in which administration of the therapeutically active agent is beneficial.

According to some of any of the embodiments described herein relating to treating a condition, comprises nasal administration of the composition.

According to some of any of the embodiments described herein relating to nasal administration, the nasal administration is for delivering the therapeutically active agent to the brain.

According to some of any of the embodiments described herein relating to nasal administration, an average diameter of nanoparticles comprising a polyanhydride as described herein is in a range of from 200 nm to 600 nm.

According to some of any of the embodiments described herein relating to nasal administration, the nanoparticles comprise thyrotropin-releasing hormone and polysebacic acid.

According to some of any of the embodiments described herein relating to treating a condition, the therapeutically active agent is thyrotropin-releasing hormone, and the condition is selected from the group consisting of a depressive disorder and epilepsy.

According to some of any of the embodiments described herein relating to a process, the solution described herein further comprises the agent dissolved in the non-aqueous solvent.

According to some of any of the embodiments described herein relating to a process, contacting is effected by slowly adding the solution to a dispersion described herein while mixing the dispersion.

According to some of any of the embodiments described herein relating to a process, the process further comprises isolating a composition described herein by precipitation and/or centrifugation.

According to some of any of the embodiments described herein relating to a process, the solution is an anhydrous solution.

According to some of any of the embodiments described herein relating to a process, the solvent comprises a homogenous mixture of a first solvent and a second solvent, wherein the agent is soluble in the first solvent and a polyanhydride described herein is soluble in the second solvent.

According to some of any of the embodiments described herein relating to a process, the process further comprises mixing a first solution comprising the agent dissolved in a first solvent with a second solution comprising a polyanhydride dissolved in a second solvent to obtain the anhydrous solution.

According to some of any of the embodiments described herein relating to a process, the first solvent is selected from the group consisting of acetone or an alcohol.

According to some of any of the embodiments described herein relating to a process, the solvent comprises a chlorinated aliphatic hydrocarbon.

According to some of any of the embodiments described herein relating to a process, the process further comprises adding a surfactant to at least one of the solvent and the anti-solvent.

According to some of any of the embodiments described herein relating to a process, the process further comprises contacting the anti-solvent with water-soluble particles described herein which comprise at least one water-soluble compound which is insoluble in the anti-solvent.

According to some of any of the embodiments described herein relating to a process, the anti-solvent is characterized by a boiling point of below 100° C. at atmospheric pressure.

According to some of any of the embodiments described herein relating to a process, the anti-solvent is heptane.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

(FIG. 5A), 2-8° C. (FIG. 5B) or −20° C. (FIG. 5C) for 1 month (circles), 3 months (triangles) or 6 months (stars), or without prior storage (squares).

(FIG. 6A) or −20° C. (FIG. 6B) for 1 month (circles), 3 months (triangles) or 6 months (stars), or without prior storage (squares).

DESCRIPTION OF SPECIFIC EMBODIMENTS OF THE INVENTION

Figure 1A:
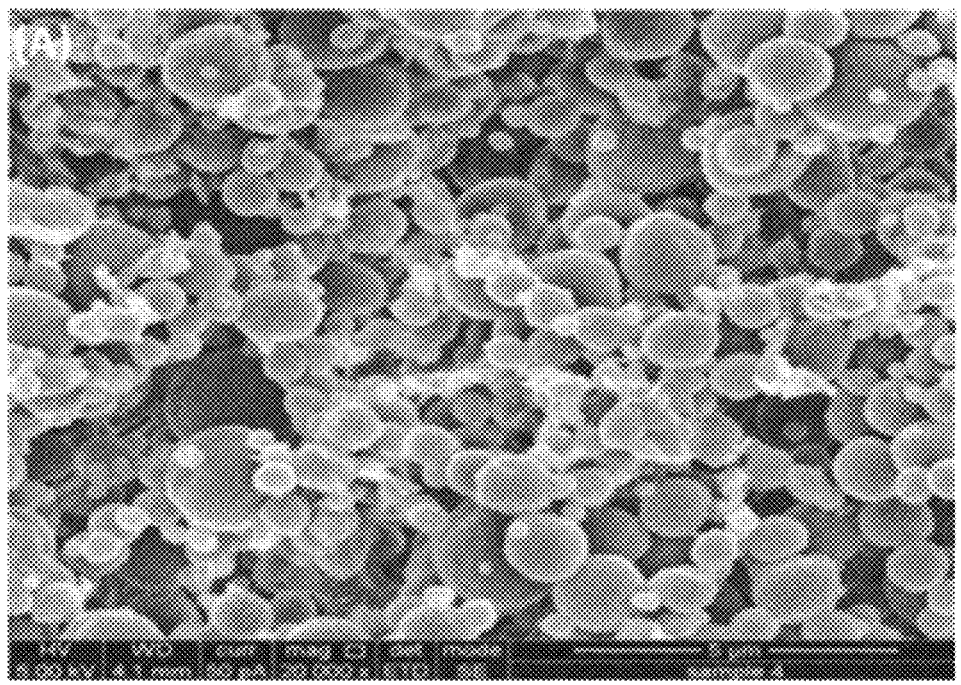
FIGS. 1A and 1B present scanning electron microscopy images of exemplary PSA nanoparticles (FIG. 1A) and TRH-loaded PSA nanoparticles (FIG. 1B), prepared in heptane, according to some embodiments of the invention.

The present invention, in some embodiments thereof, relates to delivery systems, and more particularly, but not exclusively, to lipid and/or polymeric nanoparticles usable for incorporating therein, and delivering, agents such as therapeutically active agents (drugs), such as therapeutic peptides, and to formulations containing these nanoparticles.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have considered that a major obstacle in the preparation of nanoparticles is that their isolation from the preparation media tends to involve filtration and/or strong centrifugation process which suffers from low yield and can affect the quality of the nanoparticles. Furthermore, the isolated nanoparticles may aggregate or stick to each other, especially over time during storage, without the ability to efficiently re-disperse them as a uniform dispersion, at least without intensive homogenization. This limitation is particularly acute in therapeutic applications when preparing single dosage units of nanoparticles in bottles by adding water to disperse the formulation prior to administration (e.g., intravenous injection), as failure to sufficiently disperse aggregated particles can clog a needle and/or harm a patient.

The present inventors have further considered that another significant problem obstacle in the preparation of nanoparticles is that the processes tend to require a high shear force (e.g., homogenization) to obtain nanoparticles, especially relatively small nanoparticles. However, such forces may result in deterioration of an incorporated agent (e.g., peptides, proteins or nucleotide based agents) and/or may affect the carrier.

Following laborious experimentation, the inventors have surprisingly uncovered that nanoprecipitation provides better loading of drugs (including hydrophilic drugs) into nanoparticles than do emulsion techniques (which are usually considered more suitable for hydrophilic drugs), without requiring application of a potentially deleterious high shear force.

The inventors have further uncovered that aggregation of nanoparticles prepared in such a manner can be overcome by addition of a water-soluble compound, which facilitates reliable dispersion of the nanoparticles upon contact with water.

The inventors have further uncovered that nanoprecipitation (optionally including addition of the abovementioned water-soluble compound) can be effected under anhydrous conditions, allowing the inclusion in nanoparticles of water-sensitive components such as polyanhydrides.

While reducing the present invention to practice, the inventors have prepared nanoparticles loaded with a wide variety of different drugs, by nanoprecipitation under anhydrous conditions, using various polymers, including polyanhydrides. The inventors have further utilized particles of sugars such as mannitol in combination with various nanoparticles, thereby resulting in effective re-dispersion of the nanoparticles upon contact with water. The nanoparticles were further shown to be stable under storage and to release incorporated drugs in a controlled manner.

According to an aspect of some embodiments of the invention, there is provided a composition comprising a plurality of nanoparticles, at least a portion of the nanoparticles comprising a lipid and/or polymer, and an agent incorporated in the lipid and/or polymer, wherein the lipid and/or polymer is water-insoluble.

In some of any of the embodiments of the invention relating to a composition comprising nanoparticles, the nanoparticles are associated with (optionally attached to) a surface of water-soluble particles (which may be nanoparticles and/or larger particles) which comprise at least one water-soluble compound.

Herein, the term "nanoparticle" refers to a particle having an average diameter (as determined, for example, by dynamic light scattering techniques known in the art) of no more than 1000 nm, and encompasses particles of any shape or distribution of substances. Thus, substances in a nanoparticle may optionally be homogeneously distributed or heterogeneously distributed (e.g., with a distinct core and shell).

Herein, the term "particle" (including, but not limited to nanoparticles) refers to a discrete form of a substance which is substantially solid or semi-solid.

Herein throughout, the term "insoluble" refers to a compound having a solubility of less than 1 gram per liter in an indicated solvent. For example, the term "water-insoluble" refers herein to a compound having a solubility of less than 1 gram per liter in an aqueous solution at pH 7, unless another pH is explicitly indicated.

Herein, the term "soluble" refers to a solubility of at least 1 gram per liter in an indicated solvent. For example, the term "water-soluble" refers herein to a solubility of at least 1 gram per liter in an aqueous solution at pH 7, unless another pH is explicitly indicated.

In some of any of the embodiments described herein, the composition comprising nanoparticles is in a particulate form (e.g., a powder), which may optionally be dry, or alternatively, may comprise a liquid (e.g., a solvent used in preparation of the composition).

Water-Soluble Particle:

Herein, the term "water-soluble particle" refers to a particle in which at least 1 gram of the particle dissolves upon contact with an aqueous solution at pH 7, unless another pH is explicitly indicated. Thus, the water-soluble particle both comprises at least one water-soluble compound and is structured in a manner which does not prevent dissolution in water (e.g., the water-soluble compound(s) is not enveloped by a water-insoluble material).

As discussed herein, according to some embodiments, nanoparticles comprising a lipid and/or polymer are associated with a surface of water-soluble particles.

Herein, the phrase "associated with" means that the nanoparticles are in contact with the surface, and/or bound to the surface by physical and/or chemical interactions, for example, by covalent and/or non-covalent bonding (e.g., hydrogen bonds, van der Waals bonds, electrostatic interaction, and/or hydrophobic interaction). "Contact" with a surface may comprise direct contact and/or indirect contact wherein an intermediate substance (e.g., a solvent layer) of no more than 100 nm in width (optionally no more than 10 nm in width) lies between the nanoparticles and surface (e.g., the intermediate substance being in direct contact with and/or attached to both the nanoparticles and the surface).

In some of any of the embodiments described herein, an intermediate substance, if present, is not a binder, that is, it is not a chemical substance such as a polymeric substance that is adhered or covalently attached to both the nanoparticles and the surface.

In some of any of the respective embodiments described herein, at least 50 weight percents of the water-soluble particle comprise one or more water-soluble compound(s) (according to any of the respective embodiments described herein). That is, the water-soluble particle is composed, in at least 50 weight percents thereof, of the water-soluble compound(s). In some embodiments, the water-soluble compound is at least 60 weight percents of the water-soluble particle. In some embodiments, the water-soluble compound is at least 70 weight percents of the water-soluble particle. In some embodiments, the water-soluble compound is at least 80 weight percents of the water-soluble particle. In some embodiments, the water-soluble compound is at least 90 weight percents of the water-soluble particle. In some embodiments, the water-soluble compound is at least 95 weight percents of the water-soluble particle. In some embodiments, the water-soluble compound is at least 98 weight percents of the water-soluble particle. In some embodiments, the water-soluble compound is at least 99 weight percents of the water-soluble particle.

Examples of suitable water-soluble compounds include, without limitation, saccharides (e.g., monosaccharides, disaccharides, trisaccharides, oligosaccharides and polysaccharides), alcohols (having one or more hydroxy (—OH) groups), salts (e.g., NaCl) and water-soluble polymers (e.g., hydrophilic or amphiphilic polymers such as, but not limited to, polyethylene glycol).

In some of any of the respective embodiments, the water-soluble compound comprises at least two hydroxy groups as in the case of, for example, a saccharide or a sugar alcohol.

Examples of suitable saccharides include, without limitation, monosaccharides such as dextrose, disaccharides such as sucrose or trehalose.

Herein, the term "sugar alcohol" refers to any compound corresponding to a saccharide in which the oxo group(s) of the saccharide has been replaced by hydroxy (corresponding to addition of two hydrogen atoms to the oxo group(s)).

Examples of suitable sugar alcohols include, without limitation, ethylene glycol, glycerol, erythritol, threitol, arabitol, xylitol, ribitol, mannitol, sorbitol, galactitol, fucitol, iditol, volemitol, maltitol, lactitol, and maltotriitol. Mannitol is an exemplary sugar alcohol.

In some of any of the respective embodiments, the saccharide or sugar alcohol comprises from 5 to 7 carbon atoms, optionally 6 carbon atoms.

In some of any of the respective embodiments described herein, a density of the water-soluble particles is at least 1 gram/liter. In some embodiments, the density is at least 1.1 gram/liter. In some embodiments, the density is at least 1.2 gram/liter. In some embodiments, the density is at least 1.3 gram/liter. In some embodiments, the density is at least 1.4 gram/liter. In some embodiments, the density is at least 1.5 gram/liter.

In some of any of the respective embodiments described herein, a density of the water-soluble particles is greater than that of the lipid and/or polymer of the nanoparticles, for example, by at least 0.2 gram/liter, at least 0.3 gram per liter, or more.

Without being bound by any particular theory, it is believed that a relatively high density of a water-soluble particle facilitates separation of associated nanoparticles, e.g., by sedimentation and/or gentle centrifugation.

In some of any of the respective embodiments described herein, an average size of the water-soluble particles (according to any of the respective embodiments described herein) is no more than 1000 μm (1 mm). In some embodiments, the average size is no more than 500 μm. In some embodiments, the average size is no more than 250 μm. In some embodiments, the average size is no more than 100 μm. In some embodiments, the average size is no more than 50 μm. In some embodiments, the average size is no more than 25 μm. In some embodiments, the average size is no more than 10 μm. In some embodiments, the average size is no more than 5 μm. In some embodiments, the average size is no more than 2.5 μm. In some embodiments, the average size is no more than 1 μm.

In some of any of the embodiments described herein, an average size of the water-soluble particles (according to any of the respective embodiments described herein) is at least 250 nm, for example, from 250 nm to 1000 μm, from 250 nm to 500 μm, from 250 nm to 250 μm, from 250 nm to 100 μm, from 250 nm to 50 μm, from 250 nm to 25 μm, from 250 nm to 10 μm, from 250 nm to 5 μm, from 250 nm to 2.5 μm, or from 250 nm to 1 μm.

In some of any of the embodiments described herein, an average size of the water-soluble particles (according to any of the respective embodiments described herein) is at least 500 nm, for example, from 500 nm to 1000 μm, from 500 nm to 500 μm, from 500 nm to 250 μm, from 500 nm to 100 μm, from 500 nm to 50 μm, from 500 nm to 25 μm, from 500 nm to 10 μm, from 500 nm to 5 μm, or from 500 nm to 2.5 μm.

In some of any of the embodiments described herein, an average size of the water-soluble particles (according to any of the respective embodiments described herein) is at least 1 μm, for example, from 1 μm to 1000 μm, from 1 μm to 500 μm, from 1 μm to 250 μm, from 1 μm to 100 μm, from 1 μm to 50 μm, from 1 μm to 25 μm, from 1 μm to 10 μm, or from 1 μm to 5 μm.

In some of any of the embodiments described herein, an average size of the water-soluble particles (according to any of the respective embodiments described herein) is at least 2.5 μm, for example, from 2.5 μm to 1000 μm, from 2.5 μm to 500 μm, from 2.5 μm to 250 μm, from 2.5 μm to 100 μm, from 2.5 μm to 50 μm, from 2.5 μm to 25 μm, or from 2.5 μm to 10 μm.

Without being bound by any particular theory, it is believed that smaller sizes of water-soluble particles (e.g., 50 μm or less, according to any of the respective embodiments described herein) are associated with a higher total surface area (for a given weight of particles), thereby facilitating association of nanoparticles with a surface of the water-soluble particles. It is further believed that water-soluble particles which are larger than the nanoparticles (e.g., particles of at least 250 nm, at least 500 nm, or at least 1000 nm in size, according to any of the respective embodiments described herein) are particularly useful in separating associated nanoparticles, e.g., by sedimentation and/or gentle centrifugation.

Association of nanoparticles to the water-soluble particles and/or separation of nanoparticles may optionally be enhanced by using a suitable ratio of water-soluble particles to nanoparticles.

In some of any of the embodiments described herein, a weight ratio of the water-soluble particles to the nanoparticles comprising a lipid and/or polymer (according to any of the respective embodiments described herein) is at least 1:1 (i.e., the weight of the water-soluble particles is at least equal to that of the nanoparticles), for example, in a range of from 1:1 to 1000:1, from 1:1 to 300:1, from 1:1 to 100:1, or from 1:1 to 30:1.

In some embodiments, the weight ratio is at least 2:1 (the weight of the water-soluble particles is at least twice that of the nanoparticles), for example, in a range of from 2:1 to 1000:1, from 2:1 to 300:1, from 2:1 to 100:1, or from 2:1 to 30:1.

In some embodiments, the weight ratio is at least 3:1 (water-soluble particles:nanoparticles), for example, in a range of from 3:1 to 1000:1, from 3:1 to 300:1, from 3:1 to 100:1, or from 3:1 to 30:1.

In some embodiments, the weight ratio is at least 5:1 (water-soluble particles:nanoparticles), for example, in a range of from 5:1 to 1000:1, from 5:1 to 300:1, from 5:1 to 100:1, or from 5:1 to 30:1.

In some embodiments, the weight ratio is at least 10:1 (water-soluble particles:nanoparticles), for example, in a range of from 10:1 to 1000:1, from 10:1 to 300:1, from 10:1 to 100:1, or from 10:1 to 30:1.

As exemplified herein, water-soluble particles such as described herein (according to any of the respective embodiments) facilitate dispersion of associated nanoparticles upon contact of the composition comprising the water-soluble particles and nanoparticles with water.

In some of any of the respective embodiments, upon contact of the composition comprising nanoparticles and water-soluble particles (according to any of the respective embodiments) with water (e.g., double distilled water), the nanoparticles disperse within no more than two minutes (with mixing). The volume of water contacted with the composition is a volume sufficient to dissolve the water-soluble compound without reaching saturation. In exemplary embodiments, the volume of the water is 4 ml per mg of total dry weight of the nanoparticles and water-soluble particles (e.g., 20 ml water per 5 mg particles).

Nanoparticle:

In some of any of the embodiments described herein, an average size of nanoparticles comprising a lipid and/or polymer and incorporated agent (according to any of the respective embodiments described herein) is no more than 800 nm. In some embodiments, the average size is no more than 600 nm. In some embodiments, the average size is no more than 500 nm. In some embodiments, the average size is no more than 400 nm. In some embodiments, the average size is no more than 300 nm. In some embodiments, the average size is no more than 200 nm.

Without being bound by any particular theory, it is believed that smaller sizes of nanoparticles (e.g., 600 nm or less, optionally 400 nm or less, according to any of the respective embodiments described herein) are more suitable for passing through barriers, for example, passing through cell membranes when used in pharmaceutical applications.

In some of any of the embodiments described herein, an average size of nanoparticles comprising a lipid and/or polymer and incorporated agent (according to any of the respective embodiments described herein) is at least 10 nm, for example, from 10 to 1000 nm, from 10 nm to 800 nm, from 10 nm to 600 nm, from 10 nm to 500 nm, from 10 nm to 400 nm, from 10 nm to 300 nm, or from 10 nm to 200 nm.

In some of any of the embodiments described herein, an average size of nanoparticles comprising a lipid and/or polymer and incorporated agent (according to any of the respective embodiments described herein) is at least 30 nm, for example, from 30 to 1000 nm, from 30 nm to 800 nm, from 30 nm to 600 nm, from 30 nm to 500 nm, from 30 nm to 400 nm, from 30 nm to 300 nm, or from 30 nm to 200 nm.

In some of any of the embodiments described herein, an average size of nanoparticles comprising a lipid and/or polymer and incorporated agent (according to any of the respective embodiments described herein) is at least 100 nm, for example, from 100 to 1000 nm, from 100 nm to 800 nm, from 100 nm to 600 nm, from 100 nm to 500 nm, from 100 nm to 400 nm, from 100 nm to 300 nm, or from 100 nm to 200 nm.

In some of any of the embodiments described herein, an average size of nanoparticles comprising a lipid and/or polymer and incorporated agent (according to any of the respective embodiments described herein) is at least 200 nm, for example, from 200 to 1000 nm, from 200 nm to 800 nm, from 200 nm to 600 nm, from 200 nm to 500 nm, from 200 nm to 400 nm, or from 200 nm to 300 nm.

The lipid and/or polymer according to any of the respective embodiments described herein may optionally comprise at least 50 weight percents of the nanoparticles, optionally at least 60 weight percents of the nanoparticles, optionally at least 70 weight percents of the nanoparticles, optionally at least 80 weight percents of the nanoparticles, and optionally at least 90 weight percents of the nanoparticles. In some embodiments, the nanoparticles consist essentially of the lipid and/or polymer and the agent(s) incorporated therein (according to any of the respective embodiments described herein).

In some of any of the respective embodiments described herein, the lipid and/or polymer is a solid (when substantially pure) at 25° C. and/or 37° C., for example, having a melting point below 25° C. or below 37° C.

In some of any of the respective embodiments described herein, the lipid and/or polymer is biodegradable, for example a biodegradable solid (e.g. at 25° C. and/or 37° C.).

Herein, the term "biodegradable" describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 30 weight percent of the substance decompose within a time period shorter than one year.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

Examples of biodegradable polymers include, for example, polylactides, poly(D,L-lactide-co-glycolide)s, polyglycolides, poly(lactic acid)s, poly(glycolic acid)s, poly (D,L-lactic acid-co-glycolic acid)s, polycaprolactone), poly (hydroxybutyric acid), and poly(amino acid)s, polyorthoesters, polyetheresters, polyphosphazines, polyanhydrides, polyesteramides, poly(alkyl cyanoacrylate)s, and blends and copolymers thereof.

It is expected that during the life of a patent maturing from this application many relevant biodegradable polymers will be developed and the scope of the term "biodegradable" is intended to include all such new technologies a priori.

Examples of lipids which may be included in a nanoparticle described herein include, without limitation, triglycerides, fatty acids, fatty alcohols, and fatty acid esters (i.e., an ester of a fatty acid and an alcohol). Fatty acid esters may optionally be in a form of a triglyceride, a diglyceride, a monoglyceride and a wax.

Examples of polymers which may be included in a nanoparticle described herein include, without limitation, polyanhydrides, polyesters, polyethers (e.g., polyethylene glycol), and copolymers thereof (e.g., a copolymer of a polyanhydride and/or a polyester with a polyethylene glycol).

Herein, the term "polyanhydride" refers to a polymer comprising a structure:

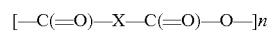

wherein n is an integer of at least 2 (e.g., from 2 to 10,000 or from 2 to 1,000), optionally at least 5, and optionally at least 10; and X is absent or is any chemical moiety, optionally a hydrocarbon, for example, a branched or linear hydrocarbon of from 1 to 20 carbon atoms in length, optionally from 4 to 12 carbon atoms in length (length referring to the shortest distance separating the carboxyl groups).

The above structure corresponds to a repeating (with n repetitions) residue of a dicarboxylic acid monomer. The residues may be of the same dicarboxylic acid monomer or different dicarboxylic acid monomers.

Examples of suitable dicarboxylic acid monomers include, without limitation, linear aliphatic dicarboxylic acids, such as malonic acid, succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, and thapsic acid; and aromatic dicarboxylic acids such as bis-carboxyphenoxyalkanes (e.g., 1,3-bis-carboxyphenoxypropane or 1,6-bis-carboxyphenoxyhexane).

Sebacic acid is an exemplary dicarboxylic acid monomer. Polyanhydrides comprising sebacic acid monomers may be polysebacic acid or copolymers thereof, for example, poly (1,3-bis-carboxyphenoxypropane-co-sebacic acid) (P(CPP:SA)).

In some of any of the embodiments described herein relating to a water-soluble compound, the polymer in the nanoparticle comprises a polyanhydride. In some embodiments, the water-soluble compound is mannitol. In some embodiments, the water-soluble compound is mannitol and the polyanhydride is polysebacic acid.

The polyesters are optionally enzymatically degradable in vivo. Such polyesters may optionally release an agent gradually, yet be sufficiently degradable as to leave no toxic residue.

Examples of polyesters include, without limitation, polymers (and copolymers) of hydroxycarboxylic acids (including lactones or lactides thereof), for example, lactic acid (D-lactic acid and/or L-lactic acid), glycolic acid, and caprolactone. Polylactic acid and copolymers of lactic acid and glycolic acid (PGLA) are exemplary polyesters.

Incorporated Agent:

In some of any of the embodiments described herein, the agent is water-soluble, as defined herein. In some such embodiments, a water-solubility of the agent (in an aqueous solution at pH 7) is at least 3 grams per liter. In some embodiments, the water-solubility of the agent is at least 10 grams per liter. In some embodiments, the water-solubility of the agent is at least 30 grams per liter. In some embodiments, the water-solubility of the agent is at least 100 grams per liter. In some embodiments, the water-solubility of the agent is at least 300 grams per liter.

In some of any of the embodiments described herein, a concentration of the agent in the nanoparticles comprising a lipid and/or polymer and the agent is at least 2 weight percents. In some embodiments, a concentration of the agent in the nanoparticles is at least 3 weight percents. In some embodiments, a concentration of the agent in the nanoparticles is at least 4 weight percents. In some embodiments, a concentration of the agent in the nanoparticles is at least 5 weight percents. In some embodiments, a concentration of the agent in the nanoparticles is at least 6 weight percents. In some embodiments, a concentration of the agent in the nanoparticles is at least 7 weight percents. In some embodiments, a concentration of the agent in the nanoparticles is at least 8 weight percents. In some embodiments, a concentration of the agent in the nanoparticles is at least 9 weight percents. In some embodiments, a concentration of the agent in the nanoparticles is at least 10 weight percents. In some embodiments, a concentration of the agent in the nanoparticles is at least 12 weight percents. In some embodiments, a concentration of the agent in the nanoparticles is at least 14 weight percents. In some embodiments, a concentration of the agent in the nanoparticles is at least 16 weight percents. In some embodiments, a concentration of the agent in the nanoparticles is at least 18 weight percents. In some embodiments, a concentration of the agent in the nanoparticles is at least 20 weight percents. In some embodiments, the agent is a water-soluble agent with a water-solubility according to any of the respective embodiments described herein.

In some of any of the embodiments described herein, a concentration of the agent in the nanoparticles comprising a lipid and/or polymer and the agent ranges from 1 to 50, or from 1 to 40, or from 1 to 30, or from 2 to 30, or from 2 to 20, or from 3 to 30, or from 5 to 30, or from 2 to 40, or from 3 to 40, or from 5 to 40, or from 1 to 20, or from 2 to 20, weight percents, including any intermediate values and subranges therebetween.

In some of any of the embodiments described herein, the agent is a therapeutically active agent, for example, a water-soluble therapeutically active agent featuring a water-solubility according to any of the respective embodiments described herein.

Examples of therapeutically active agents which may be incorporated into nanoparticles according to any of the respective embodiments described herein include, without limitation, biomolecules such as peptides, polypeptides, oligonucleotides, polynucleotides and small molecules (organic substances which can be naturally-occurring or synthetically prepared, for example, non-peptidic drugs). Each of the aforementioned agents may optionally be water-soluble, according to any of the respective embodiments described herein. In some embodiments, the therapeutically active agent is a peptide or polypeptide. Peptides are exemplary agents for incorporation into nanoparticles described herein.

Herein, a "peptide" refers to a molecule comprising a backbone of 2 to 20 amino acid residues, and a "polypeptide" refers to a molecule comprising a backbone of more than 20 amino acid residues.

Examples of suitable peptide or polypeptide agents include, without limitation, thyrotropin-releasing hormone (TRH), gonadotropin-releasing hormone (LHRH), oxytocin, insulin, and corticotropin (ACTH).

Herein, an "oligonucleotide" refers to a molecule comprising a backbone of 2 to 20 nucleotide monomers, and a "polynucleotide" refers to a molecule comprising a backbone of more than 20 nucleotide monomers.

Herein and in the art, a "small molecule" agent refers to an agent having a molecular weight of no more than 900 Da. In some embodiments, a small molecule has a molecular weight of no more than 500 Da.

Examples of suitable small molecule agents include, without limitation, steroids (e.g., dexamethasone), cannabidiol, tetrahydrocannabinol, rapamycin, anti-inflammatory agents, and anti-microbial agents such as, for example, antibiotics.

Non-limiting examples of antimicrobial and antibiotic agents that are suitable for use in this context of the present invention include, without limitation, mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12,14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, azanidazole, azidamfenicol, azidocillin, azithromycin, azlocillin, aztreonam, bacampicillin, bacitracin, bacitracin zinc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefmenoxime, cefmetazole, cefmetazole sodium, cefminox, cefminox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin cla, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin A5, leucomycin A6, leucomycin A7, leucomycin A8, leucomycin A9, levofloxacin, lincomycin, lincomycin hydrochloride, linezolid, liranaftate, l-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, ornidazole, orthophenylphenol, oxacillin, oxacillin sodium, oxiconazole, oxiconazole nitrate, oxoferin, oxolinic acid, oxychlorosene, oxytetracycline, oxytetracycline calcium, oxytetracycline hydrochloride, panipenem, paromomycin, paromomycin sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium—tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin B1, polynoxylin, povidone-iodine, propamidin, propenidazole, propicillin, propicillin potassium, propionic acid, prothionamide, protiofate, pyrazinamide, pyrimethamine, pyrithion, pyrrolnitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfonamides, sultamicillin, sultamicillin tosilate, tacrolimus, talampicillin hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, thiomersal, thiram, thymol, tibezonium iodide, ticarcillin, ticarcillin—clavulanic acid mixture, ticarcillin disodium, ticarcillin monosodium, tilbroquinol, tilmicosin, tinidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibornol and zinc undecylenate.

It is expected that during the life of a patent maturing from this application many relevant agents will be developed and the scope of the terms "agent" and "therapeutically active agent" is intended to include all such new technologies a priori.

In some of any of the embodiments described herein, the nanoparticles comprise thyrotropin-releasing hormone (TRH) and the water-soluble particles comprise mannitol. In some exemplary embodiments, the nanoparticles comprise thyrotropin-releasing hormone (TRH) and polysebacic acid, and the water-soluble particles comprise mannitol.

An agent (e.g., therapeutically active agent) may undergo release from the nanoparticles by desorption of the agent at a surface of the nanoparticle, by diffusion of the agent through the lipid and/or polymer, and/or by erosion of the lipid and/or polymer (e.g., physical erosion and/or erosion associated with chemical degradation, such as hydrolysis).

The terms "peptide" and "polypeptide", as used herein, encompass native peptides/polypeptides (either degradation products, synthetically synthesized peptides/polypeptides or recombinant peptides/polypeptides) and peptidomimetics (typically, synthetically synthesized peptides/polypeptides), as well as peptoids and semipeptoids which are peptide/polypeptide analogs, which may have, for example, modifications rendering the peptides/polypeptides more stable while in a body or more capable of penetrating into cells.

Such modifications include, but are not limited to N terminus modification, C terminus modification, peptide bond modification, backbone modifications, and residue modification.

Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide or polypeptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide/polypeptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides/polypeptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnrnhis | L-N-methylhistidine | Nmhis |
| D-N-methylisoleucine | Dnmile | L-N-methylisoleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |

TABLE 2-continued

| Non-conventional amino acid | Code | Non-conventional amino acid | Code |
|---|---|---|---|
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptide and polypeptides of some embodiments of the invention are preferably utilized in a linear form, although it will be appreciated that in cases where cyclization does not severely interfere with peptide characteristics, cyclic forms of the peptide/polypeptide can also be utilized. Cyclosporins (e.g., cyclosporin A) are non-limiting examples of therapeutically active cyclic peptides.

Since the present peptides/polypeptides are preferably utilized in therapeutics or diagnostics which require the peptides/polypeptides to be in soluble form, the peptides/polypeptides of some embodiments of the invention preferably include one or more non-natural or natural polar amino acids, including but not limited to serine and threonine which are capable of increasing solubility due to their hydroxyl-containing side chain.

The peptides or polypeptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide/polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide/polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth.

Further description of peptide/polypeptide synthesis is disclosed in U.S. Pat. No. 6,472,505.

A preferred method of preparing the peptide and/or polypeptide agents of some embodiments of the invention involves solid phase peptide synthesis.

Large scale peptide synthesis is described by Andersson [Biopolymers 2000, 55(3):227-50].

Process:

According to an aspect of some embodiments of the invention, there is provided a process for preparing nanoparticles, optionally in a form of a composition comprising a plurality of nanoparticles according to any of the respective embodiments described herein.

The process comprises contacting a solution (optionally an anhydrous solution) which comprises a lipid and/or polymer (according to any of the respective embodiments described herein) dissolved in a non-aqueous solvent, with an anti-solvent, that is, a solvent (optionally an anhydrous solvent) in which the lipid and/or polymer, and the agent to be incorporated in the lipid and/or polymer (according to any of the respective embodiments described herein) are each insoluble (as defined herein). The solvent of the solution and the anti-solvent are soluble in one another, and preferably miscible with one another. In some embodiments, the solution comprising a lipid and/or polymer further comprises the agent dissolved in the non-aqueous solvent thereof.

Herein, the phrase "non-aqueous solvent" refers to a solvent wherein more than 50 weight percents of the solvent is a substance other than water, e.g., an organic substance or compound.

In some of any of the respective embodiments, at least 90 weight percents of a non-aqueous solvent is a substance or compound other than water. In some embodiments, at least 99 weight percents of a non-aqueous solvent is a substance or compound other than water.

Herein, the term "anhydrous" refers to a substance (e.g., a solvent or anti-solvent) comprising less than 0.1 weight percent water.

In some of any of the respective embodiments, an anhydrous solution, solvent and/or anti-solvent comprises less than 0.01 weight percent (100 ppm) water. In some embodiments, an anhydrous solution, solvent and/or anti-solvent comprises less than 0.001 weight percent (10 ppm) water.

In some of any of the embodiments described herein relating to a process, the polymer is a polyanhydride, e.g., according to any of the respective embodiments described herein. In some such embodiments, the solution is an anhydrous solution and the anti-solvent is an anhydrous anti-solvent.

In some of any of the embodiments relating to a process of preparing a composition comprising water-soluble particles, the solution comprising a lipid and/or polymer (according to any of the respective embodiments described herein) is contacted with a dispersion of water-soluble particles (according to any of the respective embodiments described herein) in the anti-solvent, and the water-soluble compound of the water-soluble particles is insoluble in the anti-solvent (i.e., the anti-solvent is not water).

In some of any of the respective embodiments described herein, the process further comprises (after contacting the solution with the anti-solvent) isolating the composition by precipitation and/or centrifugation. In some such embodiments, the composition comprises water-soluble particles according to any of the respective embodiments described herein.

In some of any of the respective embodiments described herein, the solvent of the solution comprises a homogenous mixture of a first solvent (which is optionally anhydrous) and a second solvent (which is optionally anhydrous), wherein the agent (e.g., a peptide or polypeptide) is soluble in the first solvent and the lipid and/or polymer (e.g., polyanhydride) is soluble in the second solvent. In some embodiments, the agent is insoluble in the second solvent (pure second solvent) and/or the lipid and/or polymer is insoluble in the first solvent (pure first solvent). In some embodiments, the first solvent (when pure) is not miscible with the anti-solvent, but the mixture of second solvent and first solvent is miscible with the anti-solvent.

In some of any of the respective embodiments, the process further comprises mixing a first solution comprising the agent dissolved in the first solvent with a second solution comprising the lipid and/or polymer (e.g., polyanhydride) dissolved in the second solvent to obtain a solution comprising the lipid and/or polymer and agent (as described herein). In some such embodiments, the solution is an anhydrous solution.

Examples of suitable solvents for use in a first solvent (according to any of the respective embodiments described herein) include, without limitation, acetone and alcohols, for example, a $C_{1-4}$-alcohol or mixture of $C_{1-4}$-alcohols. In some embodiments, the alcohol is methanol, ethanol, n-propanol and/or isopropanol. In some embodiments, the alcohol is methanol and/or ethanol. Ethanol is an exemplary first solvent (e.g., in embodiments wherein the second solvent comprises dichloromethane).

In some of any of the embodiments relating to a first solvent comprising acetone and/or an alcohol (e.g., ethanol), the agent (which is dissolved in the first solvent) is a peptide and/or polypeptide according to any of the respective embodiments described herein.

Examples of suitable solvents for use in a second solvent (according to any of the respective embodiments described herein) include, without limitation, chlorinated aliphatic hydrocarbons (optionally comprising from 1 to 4 carbon atoms). In some embodiments, the chlorinated aliphatic hydrocarbon comprises 1 or 2 carbon atoms, for example, chloromethane, dichloromethane, chloroform, tetrachloromethane, dichloroethene and/or trichloroethane. Dichloromethane and chloroform are exemplary second solvents.

Figure 8:
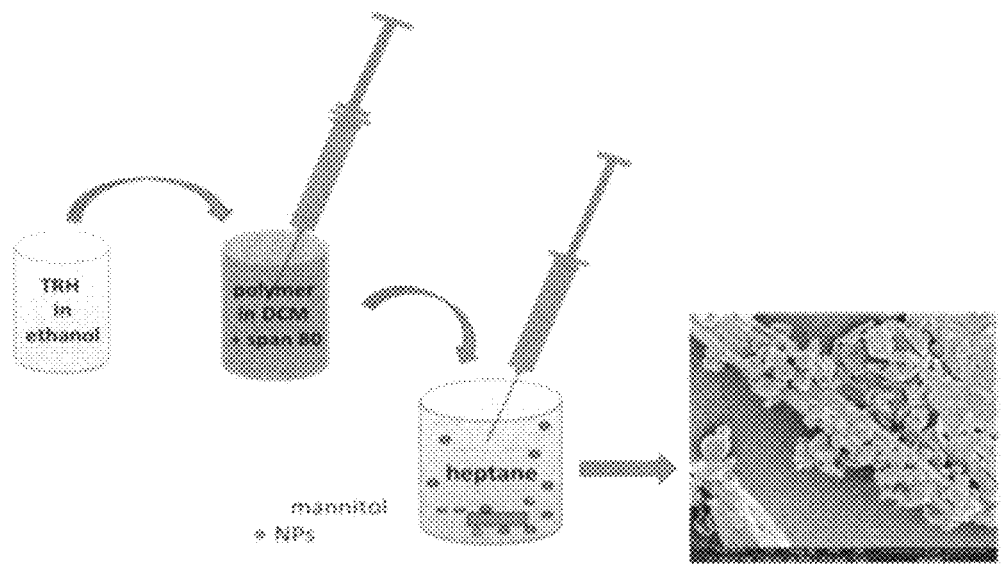
FIG. 8 schematically depicts a process for preparing a composition comprising drug-loaded nanoparticles and mannitol, according to some embodiments of the invention.

A process according to exemplary embodiments is depicted in FIG. 8. The first solvent (ethanol), agent (TRH), anti-solvent (heptane), and water-soluble compound (mannitol) depicted therein merely serve as examples, and are not to be considered limiting.

In some of any of the embodiments relating to a second solvent comprising a chlorinated aliphatic hydrocarbon (e.g., dichloromethane and/or chloroform), the lipid and/or polymer (which is dissolved in the second agent) is a polyanhydride (e.g., according to any of the respective embodiments described herein).

In some of any of the respective embodiments described herein, the anti-solvent is characterized by a boiling point of below 150° C. (at atmospheric pressure). In some embodiments, the boiling point is below 140° C. In some embodiments, the boiling point is below 130° C. In some embodiments, the boiling point is below 120° C. In some embodiments, the boiling point is below 110° C. In some embodiments, the boiling point is below 100° C. In some embodiments, the boiling point is below 90° C. In some embodiments, the boiling point is below 80° C. In some embodiments, the boiling point is below 70° C.

In general, anti-solvents with low boiling points may be more readily removed from the nanoparticle composition by evaporation (for example, under low pressure) without excessive heating or potentially damaging separation techniques such as filtration.

Examples of suitable solvents for use in an anti-solvent (according to any of the respective embodiments described herein) include, without limitation, dialkyl ethers (optionally comprising from 2 to 6 carbon atoms) and aliphatic hydrocarbons (optionally comprising from 5 to 10 carbon atoms). The aliphatic hydrocarbon may optionally be, for example, pentane (e.g., n-pentane), hexane (e.g., n-hexane), heptane (e.g., n-heptane) or a mixture of hydrocarbons, such as a petroleum ether. As exemplified herein, heptane is a particularly suitable anti-solvent. Diethyl ether is an exemplary dialkyl ether.

In some of any of the embodiments relating to an anti-solvent comprising a dialkyl ether or aliphatic hydrocarbon (e.g., diethyl ether, pentane, hexane, heptane, and/or petroleum ether), the solution comprises a chlorinated aliphatic hydrocarbon (e.g., according to any of the respective embodiments described herein), for example, as a second solvent.

In some of any of the embodiments relating to an anti-solvent comprising a dialkyl ether or aliphatic hydrocarbon (e.g., diethyl ether, pentane, hexane, heptane, and/or petroleum ether), the polymer is a polyanhydride (e.g., according to any of the respective embodiments described herein).

In some of any of the embodiments relating to an anti-solvent comprising a dialkyl ether or aliphatic hydrocarbon (e.g., diethyl ether, pentane, hexane, heptane, and/or petroleum ether), the agent is a water-soluble agent (e.g., according to any of the respective embodiments described herein), and optionally a peptide or polypeptide (e.g., TRH).

In some of any of the respective embodiments described herein, contacting the solution with the anti-solvent (optionally in a form of a dispersion of water-soluble particles) is effected by slowly adding the solution to the anti-solvent while mixing the anti-solvent, for example, at a rate of no more than 5 ml solution per minute, optionally no more than 2 ml/minute, optionally no more than 1 ml/minute, and optionally no more than 0.5 ml/minute.

In some of any of the respective embodiments described herein, the process further comprises adding a surfactant to the solvent (optionally by addition to a first solvent and/or second solvent described herein) and/or to the anti-solvent (according to any of the respective embodiments described herein). In some embodiments, the surfactant is added to the anti-solvent. In some embodiments, the anti-solvent is at a temperature of below 20° C., optionally below 15° C., optionally below 10° C., optionally below 5° C., and optionally below 0° C., upon contact with the solution with the agent and lipid and/or polymer.

In some embodiments, the surfactant has a hydrophobic nature, for example, a hydrophobic-lipophobic balance (HLB) value in a range of from 4 to 7, as determined according to standard techniques known in the art. Sorbitan monooleate is an exemplary surfactant.

In some of any of the respective embodiments described herein, the process further comprises contacting the anti-solvent with water-soluble particles which comprise at least one water-soluble compound (e.g., according to any of the embodiments described herein relating to water-soluble particles). In some embodiments, the water-soluble compound is insoluble (as defined herein) in the anti-solvent.

According to an aspect of some embodiments of the invention, there is provided a composition comprising nanoparticles obtainable by the process described herein, according to any of the respective embodiments.

Uses and Indications:

According to an aspect of some embodiments of the invention, there is provided a composition comprising nanoparticles with an incorporated therapeutically active agent, according to any of the respective embodiments described herein, for use in treating a condition in which administration of the therapeutically active agent is beneficial.

According to an aspect of some embodiments of the invention, there is provided a use of a composition comprising nanoparticles with an incorporated therapeutically active agent, according to any of the respective embodiments described herein, in the manufacture of a medicament, e.g., for treating a condition in which administration of the therapeutically active agent is beneficial.

According to an aspect of some embodiments of the invention, there is provided a method of treating a condition in a subject in need thereof, the method comprising administering a therapeutically effective amount of a composition comprising nanoparticles with an incorporated therapeutically active agent, according to any of the respective embodiments described herein (wherein administration of the therapeutically active agent is beneficial for treating the condition).

As used herein, the phrase "therapeutically effective amount" describes an amount of the compound being administered which will relieve to some extent one or more of the symptoms of the condition being treated.

Administration according to any of embodiments of any of the aspects described herein may optionally be effected by any suitable route of administration, for example, orally, by inhalation, by nasal administration, parenterally—for example by intravenous drip or by injection (e.g., intraperitoneal, subcutaneous, intramuscular or intravenous injection), transdermally, transmucosally or topically (including ophthalmic, otic, vaginal, rectal, and nasal topical administration).

In some of any of the embodiments described herein, treating comprises nasal administration of the composition. In some embodiments, nasal administration is effected once, twice or three times per day.

Herein, "nasal" administration (also referred to interchangeably as "intranasal" administration) refers to administration to at least a portion of a nasal cavity (which includes a respiratory segment and an olfactory segment), and encompasses both forms of topical administration (e.g., to regions in or near the nasal cavity) and forms of systemic administration (e.g., by entering the bloodstream and/or the central nervous system).

In some of any of the respective embodiments described herein, nasal administration (optionally directed at the olfactory segment, which is located at the roof of the nasal cavity) is for delivering the therapeutically active agent to the central nervous system, for example the brain. In some embodiments, the therapeutically active agent is an agent which does not (e.g., to a therapeutically significant extent) cross the blood-brain barrier and/or is not orally bioavailable (e.g., peptides and polypeptides which are enzymatically degraded in the digestive system).

The skilled person will be readily capable of identifying suitable therapeutically active agents which are beneficial when delivered to the brain (e.g., psychoactive agents and/or neuropeptides), as well as conditions treatable by such agents.

For example, thyrotropin-releasing hormone (TRH) may be used for treating, without limitation, brain injury, acute spinal trauma, spinocerebellar degeneration, schizophrenia, amyotrophic lateral sclerosis, depressive disorders and/or epilepsy. In some embodiments, the TRH is used for treating depressive disorders and epilepsy.

Nasal administration according to any of the respective embodiments described herein may optionally be characterized by one or more of the following advantages (while being relatively convenient and easy to effect):

a) rapid drug absorption (e.g., via highly vascularized mucosa) and onset of action;

b) enhanced bioavailability (e.g., associated with large mucosal area for absorption) and/or reduction in side effects (e.g., due to avoidance of systemic absorption);

c) facilitates self-administration (optionally enhancing compliance); and d) ability to bypass the blood-brain barrier.

In some of any of the embodiments described herein relating to nasal administration, the nanoparticles are of a sufficiently small size to be transported via the axonal pathway, e.g., through the olfactory bulb to the olfactory cortex, optionally throughout the forebrain, and optionally as far caudally as the brainstem. Alternatively or additionally, uptake and transport may optionally be effected in trigeminal neurons (e.g., via axonal transport), paracellularly in the vicinity of the Bowman's gland into cerebrovascular fluid; and/or via entry to the systemic circulation. Entry into a neuronal cell may optionally be by endocytosis.

In some of any of the embodiments described herein relating to nasal administration (e.g., for delivery to the brain), the nanoparticles comprise a polyanhydride according to any of the respective embodiments described herein. In some embodiments, the polyanhydride comprises polysebacic acid.

Without being bound by any particular theory, it is believed that the degradation time of polyanhydrides (e.g., several hours, as exemplified herein) in an aqueous environment (e.g., in the body) is particularly suitable for facilitating uptake of therapeutically active agents (e.g., peptides or polypeptides), and optionally relatively steady delivery when administered daily (e.g., once, twice or three times per day); while also allowing rapid clearance of the polymer from the body. It is further believed that a significant portion of such uptake is to tissue (e.g., olfactory nerves) which facilitates delivery to the brain and/or other portions of the central nervous system.

Alternatively or additionally, polyanhydride degradation may optionally be utilized for obtaining a relatively rapid therapeutic effect (e.g., associated with the relatively rapid degradation), such as a rapid anti-depressive or anti-epileptic effect. For example, anti-depressive agent (e.g., TRH) may optionally provide a rapid effect (e.g., in a subject exhibiting acute suicidality), and rapid anti-depressive effects may be very difficult or virtually impossible to obtain by other treatments.

In some of any of the embodiments relating to nanoparticles comprising polymers other than polyanhydrides, administration is effected no more than once per day, and optionally less frequently than once per day. In some such embodiments, the degradation time of the polymer (e.g., longer than that of polyanhydrides) is particularly suitable for facilitating sustained release of a therapeutically active agent, for example, upon oral or parenteral administration (e.g., subcutaneous injection).

According to an aspect of some embodiments of the invention, there is provided a device comprising a composition comprising nanoparticles (optionally comprising a polyanhydride) according to any of the respective embodiments described herein, the device being configured for effecting nasal administration of the composition (e.g., according to any of the respective embodiments described herein). In some embodiments, the device is configured for atomization of the composition and nasal administration upon said atomization. Such a device (and its use for nasal administration) is depicted schematically in FIG. 9.

Various modules are known in the art which are capable of effecting atomization of a liquid and/or powder composition.

The device is optionally configured for delivering a measured volume of composition and/or nanoparticles (according to any of the respective embodiments described herein).

The composition may optionally be delivered as a powder, a powder suspended in a suitable non-aqueous liquid, and/or as an aqueous suspension formed by adding aqueous medium (e.g., water) to a powder. Optionally, the device is configured for adding a measured volume of aqueous medium (e.g., water) to the composition (e.g., in powder form) prior to atomization and delivery.

The device optionally comprises an outlet configured for entry to the nose (e.g., via a nostril), for example, prior to emission of an atomized composition from the outlet. The outlet is optionally configured to direct the atomized composition preferentially toward the olfactory segment (e.g., upwards).

In some embodiments, the average particles size in the composition is suitable for transmucosal (e.g., nasal) administration, and in some embodiments, it is suitable for nasal administration for delivering the agent to the brain. Such an average particles size is known to those skilled in the art.

Formulation:

In any of the methods and uses described herein, the composition and/or nanoparticles of the present embodiments can be utilized either per se (e.g., as a dry powder) or as a part of a pharmaceutical composition that further comprises a pharmaceutically acceptable carrier.

Thus, according to additional aspects of the present invention, there is provided pharmaceutical composition, which comprises a composition and/or nanoparticles (according to any of the embodiments described herein) and a pharmaceutically acceptable carrier.

As used herein a "pharmaceutical composition" refers to a preparation of the substances presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

Proper formulation may also be dependent upon the time between formulation and administration.

For example, in some embodiments, an aqueous carrier is optionally formulated with a composition described herein shortly before administration of an obtained formulation to a subject, e.g., less than 24 hours before, optionally less than 1 hour before, optionally less than 10 minutes before, and optionally less than 1 minute before administration. Optionally, the time between formulation and administration is selected such that nanoparticles in the composition (e.g., nanoparticles comprising an anhydride) do not degrade excessively prior to administration. Alternatively or additionally, the time between formulation and administration is selected such that water-soluble particles in the composition (according to any of the respective embodiments described herein) remain undissolved (e.g., by avoiding aqueous medium) during storage.

In some embodiments, a non-aqueous carrier (e.g., a carrier in which water-soluble particles in the composition are insoluble) is optionally formulated with a composition described herein. Such a formulation may optionally be contacted with an aqueous carrier shortly before administration (e.g., as described in any of the respective embodiments), or alternatively, the formulation is administered as is, optionally using an aqueous environment in the body to react with the composition (e.g., by dissolving water-soluble particles in situ).

In some embodiments, an aqueous carrier is optionally formulated with a composition described herein a sufficient time before administration of an obtained formulation to a subject to allow dispersion of nanoparticles in the composition, for example, by dissolution of water-soluble particles in the composition. Such sufficient time may be, for example, at least 10 seconds, at least 30 seconds, at least 1 minute, at least 2 minutes, or at least 5 minutes.

The pharmaceutical composition may be formulated for administration in either one or more of routes depending on whether local or systemic treatment or administration is of choice, and on the area to be treated. Administration may be done orally, by inhalation, by nasal administration, or parenterally—for example by intravenous drip or by injection (e.g., intraperitoneal, subcutaneous, intramuscular or intravenous injection)—or topically (including ophthalmic, otic, vaginal, rectal, and nasal topical administration).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for nasal administration and/or inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of a respective condition according to any of the respective embodiments described herein.

Thus, according to an embodiment of the present invention, the pharmaceutical composition of the present invention is being packaged in a packaging material and identified in print, in or on the packaging material, for use in the treatment of a respective condition according to any of the respective embodiments described herein.

Figure 9:
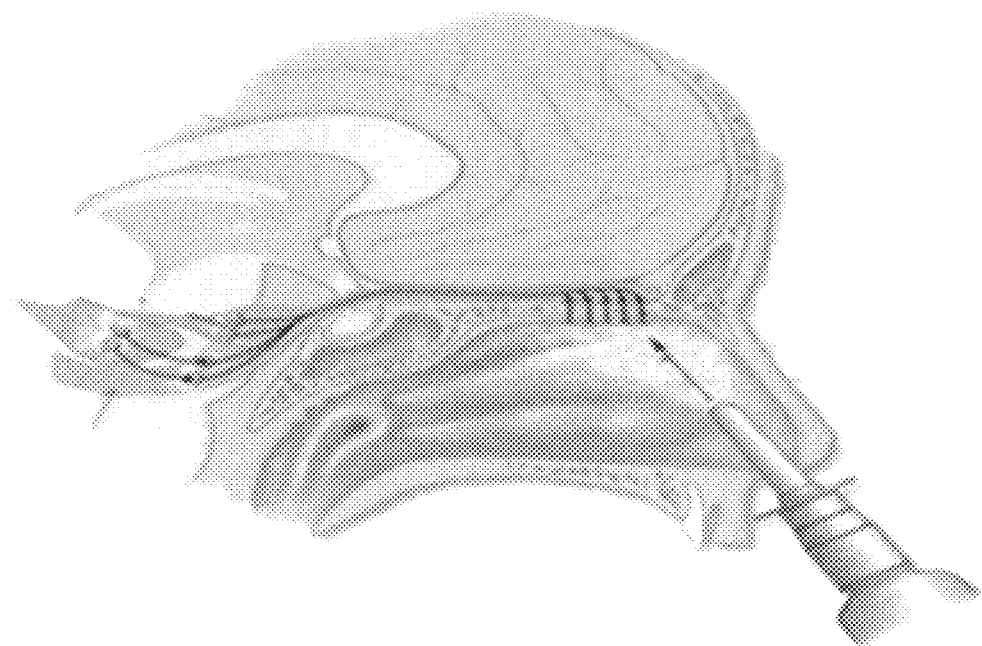
FIG. 9 depicts a device for nasal administration of nanoparticles, according to some embodiments of the invention.

According to an embodiment of the present invention, the pharmaceutical composition is suitable for providing a nasal atomization formulation, configured to be delivered to the olfactory system, e.g., by nasal administration using a device as described herein (e.g., as depicted in FIG. 9).

As used herein the term "about" refers to ±10%.

The terms "comprises", "comprising", "includes", "including", "having" and their conjugates mean "including but not limited to".

The term "consisting of" (and variants thereof) means "including and limited to".

The term "consist essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Acetic anhydride was obtained from J. T. Baker.

Acetonitrile (HPLC grade) was obtained from Bio-Lab (Israel).

Chloroform (HPLC grade) was obtained from Bio-Lab.

Chloroform-d (for NMR spectroscopy) was obtained from Sigma-Aldrich.

Citric acid was obtained from Bio-Lab.

Dichloromethane (HPLC grade) was obtained from Bio-Lab.

Ethanol (HPLC grade) was obtained from Bio-Lab.

Ethyl ether (anhydrous) was obtained from Bio-Lab.

n-Heptane was obtained from Bio-Lab.

Indocyanine green (ICG) was obtained from Sigma-Aldrich.

Mannitol was obtained from J. T. Baker.

Methanol was obtained from Bio-Lab.

1-Octanesulfonic acid sodium salt (OSA) was obtained from Sigma-Aldrich.

Petroleum ether was obtained from Bio-Lab.

Sebacic acid (SA) was obtained from Sigma-Aldrich.

Span® 80 surfactant was obtained from Sigma-Aldrich.

Tetrahydrofuran (THF) was obtained from Bio-Lab.

Thyrotropin-releasing hormone (TRH; clinical grade) was obtained from Bachem Americas, Inc.

Preparation of Poly(Sebacic Acid):

A melt condensation process was utilized, as this method has been studied extensively due to its simplicity and ability to produce high molecular weight polymers [Kumar & Langer, *Adv Drug Deliv Rev* 2002, 54:889-910; Leong et al., *Macromolecules* 1987, 20:705-712]. As depicted in Scheme 1, the dicarboxylic acid monomers are converted into a mixed anhydride of acetic acid by refluxing in excess of an acetic anhydride solution. Thereafter, the solution mixture is heated under controlled vacuum to initiate polymerization [Domb & Langer, *J Polym Sci A Polym Chem* 1987, 25:3373-3386; Sabir et al., *J Mater Sci* 2009, 44:5713-5724; Xu et al. [*Polym Bull* 2001, 46:435-442].

Sebacic acid (SA) was heated in the first step with an excess of acetic anhydride (1:5 w/v) at 140° C. for 30 minutes under reflux, with access of inert gas ($N_2$) in an oil bath. The excess acetic anhydride was then removed by a rotary vacuum evaporator at 60° C. under reduced pressure (~30 kPa). The clear viscous residue thereby obtained was polymerized in the second stage by melt condensation at 160° C. for 5 hours under a vacuum of ~2 kPa with constant stirring. The obtained poly(sebacic acid) (PSA) was stored at −20° C. in an air-tight and moisture-free compartment until use.

The PSA was characterized using Fourier transform infrared spectroscopy (FTIR), $^1$H-NMR spectroscopy, and gel permeation chromatography (GPC), as described herein.

FTIR spectra of the synthesized PSA polymer showed peaks at 2912 and 2850 $cm^{-1}$ due to methyl groups (—$CH_2$—, —$CH_3$). A typical double anhydride carbonyl (C=O) peak appeared at 1,800 and 1,740 $cm^{-1}$, which confirms the presence of anhydride bonds [Liang et al., *J Appl Polym Sci* 2013, 127:3948-3953]. Peaks at 1061 and 1030 $cm^{-1}$ correspond to symmetrical stretching vibrations of anhydride segments (C—O—C stretching).

$^1$H-NMR spectra of synthesized PSA showed a triplet at 2.43 ppm, which is due to methylene protons conjugated to the anhydride groups. An additional peak due to methyl protons in the acetic anhydride end groups was observed at 2.2 ppm. Two other peaks were observed at 1.66 and 1.31 ppm.

Gel permeation chromatography showed $M_n$ value of synthesized PSA as 4500 Da whereas the MW value was 9100 Da. The polydispersity index of the synthesized PSA was 2.02.

Fourier Transform Infrared Spectroscopy (FTIR):

FTIR spectra were recorded with a Smart iTR™ Nicolet iS10 FTIR spectrometer (Thermo Scientific) with diamond crystal. The instrument requires ~5-10 mg sample that is placed onto a crystal window and spectrum recorded. The scanning range was 400-4000 $cm^{-1}$ and the resolution was 4 $cm^{-1}$. The number of scans for each sample was set to 10.

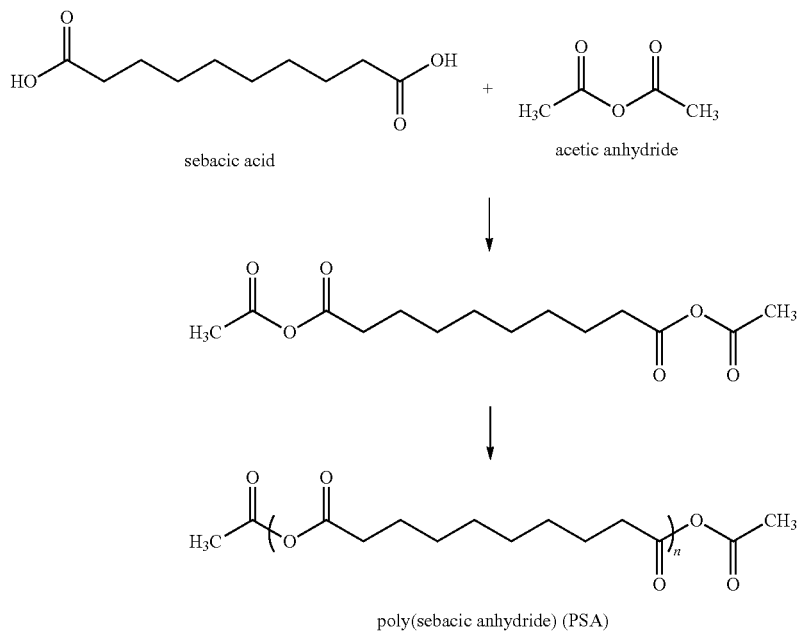

Scheme 1 poly(sebacic anhydride) (PSA)

¹H-NMR Spectroscopy:

NMR data were acquired using a Mercury™ 300 MHz NMR spectrometer (Varian). A 10 mg polymer sample was dissolved in 2 ml of deuterated chloroform (CDCl₃). The sample solution was transferred to NMR tubes of 5 mm diameter, and results were recorded as ppm relative to tetramethylsilane (TMS) taken as internal standard.

Gel Permeation Chromatography (GPC):

Molecular weight and molecular weight distribution of the synthesized polymer were determined by gel permeation chromatography (GPC) using a Waters® 717 plus auto sampler system. 5 mg polymer samples were dissolved in 2 ml chloroform. The sample was filtered through a 0.45 µm filter directly into the GPC vials. Then 100 µl of the sample solution was injected into the system consisting of a Rheodyne™ injection valve with a 20 µl loop, a linear Styragel® column HR3 (500 Å pore size, Waters, Mass.), and a Merck-Hitachi LaChrom refractive index detector L 7490. Elution was performed at 30° C. with chloroform at a flow rate of 1 ml/minute. Polystyrene standards of known molecular weight range (3470 to 54,000 Da) were employed for calibration using software from Empower Software Technologies (Murrieta, Calif.).

Determination of Drug Content and Yield:

Drug content was determined using HPLC (high performance liquid chromatography), using a LiChrospher® 100 RP-18 (5 µm) column packed in a LiChroCART® 250-4 HPLC cartridge (Merck KGaA). The chromatographic system used was a Merck-Hitachi LaChrom™ HPLC system equipped with UV detector (Model LaChrom™ L7400). The mobile phase consisted of an aqueous phase (0.05% of 1-octanesulfonic acid sodium, pH adjusted to 2.2 with 3M phosphoric acid and added 100 µL TEA per 1000 ml) and organic phase (acetonitrile) in a ratio of 90:10, used in isocratic mode. Sample injection volume was 50 µl. The analysis was carried out at 35° C. at a flow rate of 1.5 ml/minute. The effluent was monitored on a UV detector attached to the HPLC system at wavelength 215 nm.

TRH showed a retention time of 6.3 minutes under these conditions. Calibration plots were prepared in a concentration range of 1-100 µg/ml.

5 mg of dried nanoparticle were added to 1 ml double distilled water and kept for continuous shaking at 50 rotations per minute at 37° C. until the end of the experiments. Thereafter, the samples were centrifuged at 6000 rotations per minute, and the supernatant medium was analyzed to estimate the amount of TRH using reversed phase HPLC method, according to procedures such as described in Rao et al. [*Pharm Res* 1987, 4:38-41]. All experiments were performed in triplicate.

TABLE 3

Composition of exemplary TRH-loaded PSA nanoparticles

| Components | Weight (mg) | % w/w |
|---|---|---|
| PSA | 54 | 17.96 |
| Span ® 80 surfactant | 0.6 | 0.2 |
| Mannitol | 240 | 79.84 |
| TRH | 6 | 2.0 |
| Total | 300.6 | 100 |

The composition of exemplary TRH-loaded PSA nanoparticles is presented in Table 3.

The obtained nanoparticles (NPs) from each formulation were weighed, and the respective percentage yield was calculated using the following equation (1):

$$\text{Percentage yield} = \frac{\text{Wt of collected dry NPs powder obtained}}{\text{Wt of drug, polymer, surfactant and Mannitol used}} \times 100 \quad (1)$$

Based on the composition shown in Table 3, the yield of obtained nanoparticles was typically in the range of 90-95%.

Determination of Drug Loading and Entrapment Efficiency:

The drug encapsulation efficiency was determined by measuring the amount of extractable drug (e.g., TRH) in the drug-loaded PSA nanoparticles. For this, 20 mg of nanoparticles were dissolved in 5 ml of chloroform and 5 ml of DDW at pH 2.2 (acidified with dilute HCl). The mixture was mixed by vortex for 30 minutes at room temperature to facilitate extraction of the drug from the organic phase into the aqueous phase. The aqueous and organic phases were separated by centrifugation for 10 minutes at 4,000 rotations per minute at 4° C. The drug concentration was measured in triplicate by a validated in vitro HPLC method.

Drug loading and encapsulation entrapment efficiency were calculated using the following equations (2) and (3):

$$\text{Drug loading (\%)} = \frac{\text{Weight of drug in nanoparticles}}{\text{Weight of nanoparticles taken}} \times 100 \quad (2)$$

$$\text{Entrapment efficiency (\%)} = \frac{\text{Actual TRH Loaded in nanoparticles}}{\text{Theoretical THR drug in nanoparticles}} \times 100 \quad (3)$$

Determination of Particle Size and Surface Charge:

Nanoparticle size was determined using dynamic light scattering (DLS), using a Zetasizer™ Nano ZS apparatus (Malvern Instruments) equipped with inbuilt software. Nearly 1 ml of a dispersion of nanoparticles (e.g., heptane) was placed into a glass cuvette (12 mm glass cell with square aperture). Each blank nanoparticle batch was appropriately diluted with the applicable amount of heptane. The measurement angle was selected at 173 Backscatter (NIBS) in automatic selection mode. The z-average of the nanoparticles was calculated using the auto-correlation function of the intensity of light scattered from the particles, assumed to be in the spherical form by the instrument software. All measurements were conducted in triplicate at 25° C. for each batch of nanoparticles. The hydrodynamic diameter (dH) measured by this technique reflects the dimension of the nanoparticle together with solvent layers bound to its surface.

Particle Morphology:

Morphology of nanoparticles was assessed by high resolution scanning electron microscopy (SEM). For imaging of nanoparticles, dried samples were placed on double sided tape fixed on a metal stub. The metal stubs containing samples were vacuum coated with a thin layer of gold, using ion sputter with Au target assembly. The samples were analyzed using extra-high resolution scanning electron microscope (Magellan™ 400L Field Emission Scanning Electron Microscope) operated at a voltage of 5.00 kV and 2.00 kV.

In Vitro Drug Release Assay:

Release of a drug (e.g., thyrotropin-releasing hormone) from drug-loaded nanoparticles was evaluated in triplicate by adding 5 mg of the nanoparticles to 1 ml of release medium taken in Eppendorf™ tubes. Two different release media were used for the purpose: double distilled water (DDW), and 0.1 M phosphate buffer (pH 7.4±0.2). The tubes were placed into a shaker agitated at 30 rotations per minute and maintained at 37° C. At various time intervals, the tubes were withdrawn from the shaker and centrifuged at 6000 rotations per minute to separate the nanoparticles. 800 µl supernatant from the release medium was withdrawn and same amount was replaced by fresh medium. The settled nanoparticles were again dispersed into the release media and placed again into the shaker to continue the release study for the next time period. The collected sample was suitably diluted and analyzed to estimate the amount of drug released using HPLC, as described herein.

In Vitro Hydrolytic Degradation Measurement:

PSA nanoparticles were measured by FTIR spectroscopy before and after exposure to double distilled water (DDW) in a drug release study (as described herein). After completion of a 12 hour release study in DDW, the nanoparticles were centrifuged and then lyophilized for FTIR measurements. The obtained FTIR data for the anhydride and carboxylic acid group were compared in the samples for both, before and after release experiments.

Cell Line and Culture:

The A431 human epithelial squamous carcinoma cell line was used as a model cell line to understand the biological behavior of nanoparticles [Oliva et al., *Adv Nat Sci Nanosci Nanotechnol* 2018, 9:015001-015009; Amin et al., *Nano LIFE* 2014, 4:1440002-10]. These cells help identify the behavior of epithelial tissue inside the nasal cavity, which may be penetrated by nanoparticles to target the brain. A431 carcinoma cells were grown in flasks with Dulbecco's Modified Eagle's Medium (DMEM) containing 10% fetal bovine serum, 2 mM L-glutamine, 10000 U/ml penicillin and 100 mg/ml streptomycin. The cells were incubated at 37° C. with air saturated with water and 6% carbon dioxide. The growth medium was replaced every two days, and the cells were split with 0.25% trypsin once a week when they reach a density of 90%. Cells were counted using a hemocytometer. All experiments were carried out under GLP conditions in a clean room according to ISO7 requirements (10,000 particles/m$^3$) and international standard ISO 14644-1.

Cell Cytotoxicity Assay:

Cellular viability and toxicity were determined by resazurin assay, according to procedures such as described in Bonnier et al. [*Toxicology In Vitro* 2015, 29:124-131]. Resazurin (also known as Alamar Blue) is non-toxic to cells and can be used as a redox indicator that yields colorimetric change and a fluorescent signal in response to metabolic reduction in mitochondria [Vega-Avila & Pugsley, *Proc West Pharmacol Soc* 2011, 54:10-14]. NADPH or NADH converts resazurin to resorufin, which is pink and highly fluorescent. The amount of fluorescence produced is proportional to the number of living cells. The following day and the day thereafter a proliferation protocol was used with resazurin indicator: 10 µl of 10% resazurin solution was added to each well for 4 hours. The cells were then visualized using an ELISA reader (excitation wavelength=540 nm, emission wavelength=595 nm).

Comparative Example 1

Preparation of Drug-Loaded Nanoparticles by Emulsion Technique

Preparation of drug-loaded PLGA (poly(lactide-co-glycolide)) nanoparticles was attempted by a double emulsion technique. Initially, 0.5 mg of drug was dissolved in 50 µl of water and added to 0.5 ml of ethyl acetate containing 10 mg of PLGA followed by sonication for 30 seconds. This primary emulsion (water-in-oil) was added to 2 ml of 1% PVA (polyvinyl alcohol) and again sonicated for 60 seconds. The obtained emulsion was added to 25 ml of 0.1% PVA solution and stirred for 1 hour. This method resulted in precipitation of polymer to form large particles with less than 5% encapsulation yield.

The method was therefore modified by replacement of PVA solution with Tween® 80. Initially, 0.5 mg of drug was dissolved in 50 µl of water and added to 0.5 ml of ethyl acetate containing 10 mg of PLGA followed by sonication for 30 seconds. This primary emulsion (water-in-oil) was added to 2 ml of 2% Tween® 80 and again sonicated for 60 seconds. The obtained emulsion was added to 25 ml of 0.2% Tween® 80 solution and stirred for 1 hour, followed by centrifugation at 10,000 rotations per minute for 15 minutes.

Nanoparticles with 88 nm of particle size were obtained with this method. These nanoparticles were evaluated for drug loading by an indirect method which involves injecting the obtained supernatant into an HPLC column and analysis of drug content present in supernatant. Most drug was found in the supernatant, with the PLGA nanoparticles exhibiting 0.2% loading and 0.04% entrapment efficiency (with theoretical loading being 5%). Such results were considered unsatisfactory.

Comparative Example 2

Preparation of Polyester Nanoparticles by Nanoprecipitation 10 mg of PLGA (poly(lactide-co-glycolide)) and 0.5 mg of thyrotropin-releasing hormone (TRH) were dissolved in 0.2 ml of DMSO by vortex. The obtained solution was added to 4 ml of methanol under constant stirring at 1000 rpm for 1 hour. Nanoparticles of average particle size 218 nm were obtained. Drug loading of nanoparticles was determined to be 0.014%, and entrapment efficiency was 0.0028% (with theoretical loading being 5%). Such results were considered unsatisfactory.

Example 1

Preparation of Drug-Loaded Polyanhydride Nanoparticles by Nanoprecipitation with Hexane Anti-Solvent 25 mg of polymer (polysebacic acid (PSA) or (poly(1,3-bis-carboxyphenoxypropane-co-sebacic acid) (P(CPP-SA)) was dissolved in 0.5 ml of dichloromethane (DCM). 1.25 mg of thyrotropin-releasing hormone (TRH) was suspended in 0.5 ml DCM and sonicated for 1 minute, then both mixtures were mixed and injected in 50 ml of n-hexane (serving as an anti-solvent) containing 2% Span® 80 surfactant with an insulin syringe at a rate of 0.2 ml/minute. The solvent phase was added under stirring (500 rotations per minute) and homogenization (10,000 rotations per minute) which continued for 15 minutes after addition. Nanoparticles were separated by centrifugation at 4000 rotations per minute for 10 minutes and washed with 20 ml of n-hexane. The obtained nanoparticles were evaluated for size, loading, and entrapment efficiency.

One batch of PSA nanoparticles had an average size of 238 nm, with drug loading of 0.422% and entrapment efficiency of 8.44%; and another batch of PSA nanoparticles had an average size of 267 nm, with drug loading of 0.602% and entrapment efficiency of 12.04%.

One batch of P(CPP-SA) nanoparticles had an average size of 243 nm, with drug loading of 0.678% and entrapment efficiency of 13.56%; and another batch of P(CPP-SA) nanoparticles had drug loading of 0.634% and entrapment efficiency of 12.68%.

It was hypothesized that the low entrapment efficiency was associated with the in ability of DCM to solubilize the TRH. A different solvent for TRH was therefore sought.

Nanoparticles were prepared according to the abovementioned procedures, except that the TRH was dissolved in ethanol (rather than suspended in DCM), and then mixed with a polymer solution in DCM.

One batch of obtained PSA nanoparticles had an average size of 1627 nm, with drug loading of 2.7% and entrapment efficiency of 54.01%; and another batch of PSA nanoparticles had an average size of 1356 nm, with drug loading of 3.26% and entrapment efficiency of 65.36%.

One batch of obtained P(CPP-SA) nanoparticles had an average size of 1957 nm, with drug loading of 3.03% and entrapment efficiency of 60.61%; and another batch of P(CPP-SA) nanoparticles had an average size of 990 nm, with drug loading of 3.82% and entrapment efficiency of 76.51%.

These results indicate that the use of ethanol as co-solvent enhanced entrapment efficiency and drug loading.

In a similar process, 0.5 mg of aspirin was dissolved in 0.1 ml of ethanol, and mixed in 10 mg of polysebacic acid (PSA) dissolved in 0.2 ml of chloroform, and the clear solution was added slowly to 5 ml of heptane under constant stirring at 600 rotations per minute pm for 1 hour. Nanoparticles of average particle size in the range of 200-250 nm were obtained in high yield and loading. However, the isolated nanoparticles could not be re-dispersed and formed a mass that could not disperse even when applying sonication or rapid mixing.

As the above results were characterized by either large particle size or small particles which could not be separated, further modifications were investigated in order to obtain small and dispersible nanoparticles with efficient drug loading.

Example 2

Preparation of Drug-Loaded Polysebacic Acid Nanoparticles by Nanoprecipitation with Diethyl Ether Anti-Solvent and Mannitol 54 mg of polysebacic acid (PSA) was dissolved in 2.85 ml dichloromethane (DCM) with 1% w\w Span® 80 surfactant at room temperature. 6 mg of cannabidiol (CBD) was dissolved in 0.5 ml DCM and then mixed with the polymer solution. The polymer/CBD solution was loaded into a syringe with a 30 G needle and injected into diethyl ether (serving as anti-solvent) which already contained 240 mg lyophilized, ground mannitol passed through a sieve (size 60 mesh, ~1 micron in size) and fluidized by sonication, at an anti-solvent to solvent ratio of 100:1. Injection of the polymer/CBD solution was over the course of three minutes while stirring (the needle was dipped inside the anti-solvent) and then the stirring continued for 2 additional minutes. The obtained particles were removed from the anti-solvent by centrifugation and then dried under nitrogen to yield nanoparticles with an average size of 210 nm. The CBD loading and overall process yield (calculated as described in the Materials and Methods section) were both above 90%.

Example 3

Preparation of Dexamethasone-Loaded Polysebacic Acid Nanoparticles by Nanoprecipitation with Hexane Anti-Solvent and Mannitol 54 mg of polysebacic acid (PSA) was dissolved in 2.85 ml dichloromethane (DCM) with 1% w\w Span® 80 surfactant at room temperature. 6 mg of dexamethasone was dissolved in 0.5 ml DCM and then mixed with the polymer solution. The polymer/dexamethasone solution was loaded into a syringe with a 30 G needle and injected into a dispersion of 240 mg lyophilized, ground mannitol passed through a sieve (size 60 mesh, ~1 micron in size) in hexane (serving as anti-solvent), at an anti-solvent to solvent ratio of 10:1. Injection of the polymer/dexamethasone solution was over the course of three minutes while stirring (the needle was dipped inside the anti-solvent) and then the stirring continued for 2 additional minutes. The obtained particles were removed from the anti-solvent by centrifugation and then dried under nitrogen to yield nanoparticles with an average size of 240 nm. The loading and overall process yield were both above 90%.

Example 4

Preparation of Drug-Loaded Polymer Nanoparticles by Nanoprecipitation with Heptane Anti-Solvent and Mannitol 54 mg of polysebacic acid (PSA) was dissolved in 2.85 ml dichloromethane (DCM) with 1% w\w Span® 80 surfactant at room temperature. 6 mg of oxytocin was dissolved in 0.5 ml DMSO and then mixed with the polymer solution. The polymer/oxytocin solution was loaded into a syringe with a 30 G needle and injected into heptane (serving as anti-solvent) which already contained 240 mg lyophilized mannitol (~1 micron in size) fluidized by sonication, at an anti-solvent to solvent ratio of 10:1. Injection of the polymer/oxytocin solution was over the course of three minutes while stirring (the needle was dipped inside the anti-solvent) and then the stirring continued for 2 additional minutes. The obtained particles were removed from the anti-solvent by centrifugation for 5 minutes at 6,000 rotations per minutes and then dried under vacuum in a desiccator. Particles with an average size of 180 nm were obtained with both drug entrapment and overall yield being above 90%.

Upon placement of the nanoparticles in phosphate buffer (pH 7.4) at 37° C., the oxytocin was constantly released for over 12 hours, as determined by HPLC.

Aspirin was incorporated into PSA nanoparticles by a similar process, in which aspirin was dissolved in acetone, PSA was dissolved in chloroform, and the aspirin solution and PSA solution were then mixed, before being gradually added to the anti-solvent, heptane containing lyophilized mannitol. Nanoparticles precipitated onto the mannitol rods were isolated from the solution by filtration. The particle size ranged from 100 to 500 nm. The entrapment yield of aspirin was more than 90% and total yield of the process was more than 80%. The in vitro release of aspirin from the particles was gradual over the course of 24 hours.

Example 5

Preparation of Protein Hormone-Loaded Polysebacic Acid Nanoparticles by Nanoprecipitation with Heptane Anti-Solvent and Mannitol

54 mg of polysebacic acid (PSA) was dissolved in 2.85 ml dichloromethane (DCM) with 1% w\w Span® 80 surfactant at room temperature. 6 mg of luteinizing hormone-releasing hormone (LHRH; a.k.a. gonadotropin-releasing hormone or GnRH) was dissolved in 0.5 ml ethanol (waiting at least 10 minutes for dissolution) and then mixed with the polymer solution. The polymer/LHRH solution was loaded into a syringe with a 30 G needle and injected into heptane (serving as anti-solvent) which already contained 240 mg lyophilized mannitol (~1 micron in size) fluidized by sonication, at an anti-solvent to solvent ratio of 100:1. Injection of the polymer/LHRH solution was effected gradually with the needle dipped inside the anti-solvent. The obtained particles (LHRH-loaded PSA nanoparticles and mannitol particles) were isolated by precipitation and filtration. The isolated nanoparticle composite was dispersed immediately in water and analyzed for particle size. The average size was 190 nm, and the encapsulation yield and total yield were both above 90%.

Example 6

Preparation of Cyclosporin-Loaded Polysebacic Acid Nanoparticles by Nanoprecipitation with Heptane Anti-Solvent and Mannitol

54 mg of polysebacic acid (PSA) was dissolved in 2.85 ml dichloromethane (DCM) at room temperature. 6 mg of cyclosporin was dissolved in 0.5 ml ethanol and then mixed with the polymer solution. The polymer/cyclosporin solution was loaded into a syringe with a 30 G needle and injected into heptane (serving as anti-solvent) which already contained 250 mg NaCl powder, at an anti-solvent to solvent ratio of 10:1. Injection of the polymer/cyclosporin solution was over the course of two minutes while stirring.

The obtained nanoparticles had a size in a range of from 200-400 nm, and a zeta potential of −40 mV.

5 mg of the obtained nanoparticles were added to 1 ml double-distilled water (DDW) and kept for 48 hours at 37° C. (with shaking at 30 rotations per minute). Sampling was effected by sedimentation of nanoparticles by centrifugation, and replacing the medium. 800 µl of the sampled medium was diluted with an equal amount of DDW. At the end of the 48 hours, the particles were isolated by centrifugation. The medium was analyzed by HPLC, with all experiments being performed in triplicate.

Cyclosporin was constantly released from the nanoparticle for 48 hours as the PSA was gradually hydrolyzed.

Example 7

Characterization of Thyrotropin-Releasing Hormone-Loaded Polysebacic Acid Nanoparticles

54 mg PSA (prepared as described in the Materials and Methods section) with 1 mg/ml of Span® 80 surfactant and 6 mg of TRH were separately dissolved in 2.85 ml methylene chloride and 0.5 ml of ethanol, respectively. The TRH solution was then mixed into the PSA solution under constant stirring. This solution mixture (TRH+PSA) was then added very slowly to the dispersing phase (anti-solvent) using a syringe with a 30 G needle positioned directly in the medium, under moderate magnetic stirring, such that the injection lasted for three minutes. The dispersing anti-solvent medium was heptane with 240 mg of lyophilized mannitol in the present study. The optimized conditions for the preparation of the nanoparticles as well as the selection of the amount of solvent/anti-solvent, amount of mannitol and Span® 80 surfactant, are completely based on the best results after performing several repetitive trial experiments (data not shown). The anti-solvent to solvent ratio was fixed at 100:1. After complete dispersion of the TRH+PSA solution in heptane, stirring was continued for additional two minutes, and the batch was analyzed for particle size. The nanoparticles and mannitol particles were removed from the anti-solvent by centrifugation for 20 minutes at 6000 rotations per minute. The freshly formed TRH/PSA nanoparticles were then washed with distilled water to gradually remove the dispersing medium, and then dried under vacuum in a desiccator. The final product was kept in a sealed vial under a dry atmosphere at −20° C.

The TRH encapsulation efficiency in the PSA nanoparticles was determined according to procedures described in the Materials and Methods section hereinabove, and found to be about 100%.

For comparison, nanoparticles were also prepared according to similar procedures, but without TRH (blank nanoparticles), surfactant, or mannitol, and with different temperatures.

TABLE 4

Effect of process and formulation parameters on particle size and PDI of TRH-PSA NPs formulated using anti-solvent nanoprecipitation method

| Nanoparticle type | surfactant (Span ® 80) | Particle size (nm) ± S.D. | Polydispersity index ± S.D. |
|---|---|---|---|
| Blank PSA | with (in solvent) | 396.7 ± 127.16 | 0.520 ± 0.08 |
| TRH-loaded PSA | with (in solvent) | 384.1 ± 146.3 | 0.439 ± 0.13 |
| Blank PSA (optimization process) | without | 1094.2 ± 131.12 | 0.253 ± 0.056 |
| | without, in ice bath | 1585.31 ± 221.9 | 0.298 ± 0.094 |
| | with (in solvent) | 450.5 ± 99.18 | 0.311 ± 0.033 |
| | with (in anti-solvent) | 378.32 ± 157.26 | 0.276 ± 0.092 |
| | with (in anti-solvent), in ice bath | 228.40 ± 18.61 | 0.189 ± 0.121 |
| TRH-loaded PSA (optimized) | with (in anti-solvent), in ice bath | 258.0 ± 90.48 | 0.204 ± 0.033 |

As shown in Table 4, the average size of the PSA particles in the absence of a surfactant was on a scale of 1000 nm at room temperature, whereas in the presence of a surfactant (Span® 80) the average size was reduced by about 76%. As further shown therein, when the anti-solvent with surfactant was cooled (in an ice bath), the average nanoparticle size was reduced by about 86%.

As further shown therein, TRH-loaded nanoparticles prepared in cooled anti-solvent with surfactant were also small, having an average size of 258 nm. The size of TRH-loaded nanoparticles consistently differed by no more than about 12% from the size of similarly prepared blank PSA particles.

These results indicate that the surfactant reduced self-aggregation of nanoparticles, thereby maintaining a relatively small nanoparticle size.

Figure 1B:
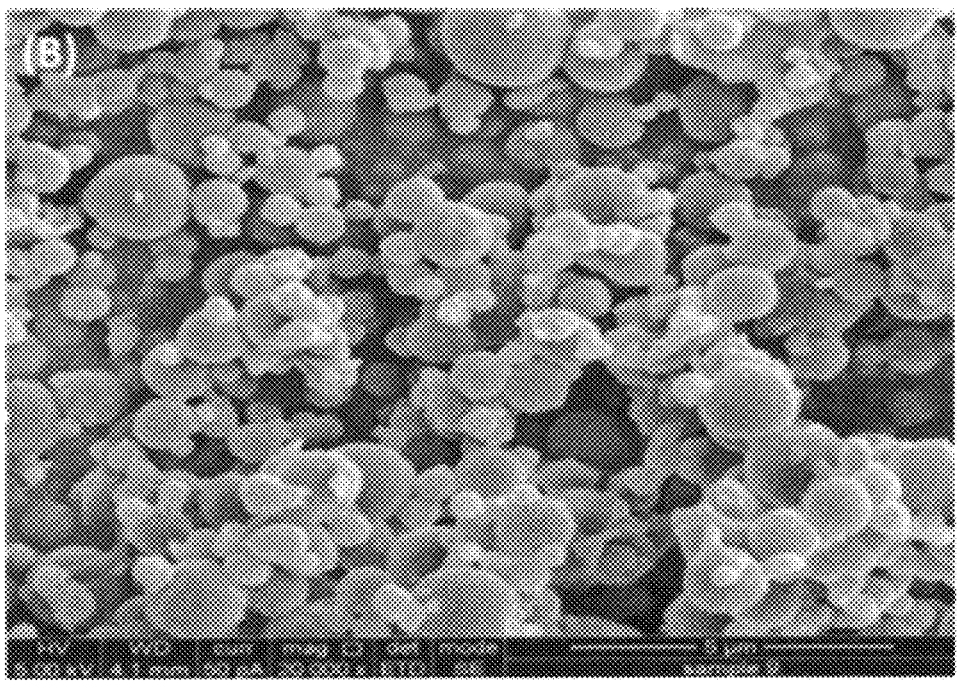

As shown in FIGS. 1A and 1B, both blank PSA nanoparticles (FIG. 1A) and TRH-loaded PSA nanoparticles (FIG. 1B) exhibited a relatively uniform and spherical shape, as observed by scanning electron microscopy; and loading with TRH did not significantly affect the size, shape or morphology of the nanoparticles relative to blank nanoparticles.

These results indicate that the methodology described herein can reliably and reproducibly form drug-loaded nanoparticles having a controlled size and shape, which is suitable, for example, for spreading uniformly over a cell membrane.

Zeta potentials for the blank PSA nanoparticles and TRH-loaded PSA nanoparticles were determined to be −44.8±1.85 mV and −41.2±3.22 mV.

These results indicate that the TRH alters the surface charge of the nanoparticles. Such a phenomenon has been reported as an indication of the drug that is encapsulated in the interior of the nanoparticles [Wang et al., *Int J Mol Sci* 2016, 17:E2012].

Without being bound by any particular theory, it is believed that under aqueous conditions the TRH is not completely available as charged cationic species; and that the histidine (His) residue in TRH is not in a protonated state, and may add an insignificant amount of partial positive charge to the molecule if protonated [Perlman et al., *J Biol Chem* 1992, 267:24413-24417].

After centrifugation, the nanoparticles prepared without mannitol in the anti-solvent were not completely separated from the anti-solvent phase.

Figure 2A:
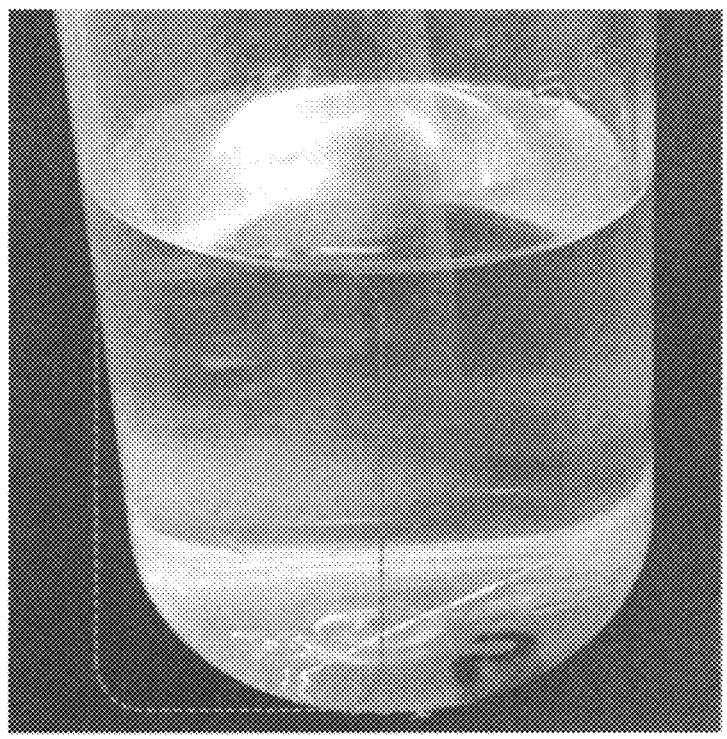
FIGS. 2A and 2B present photographic images of nanoparticles prepared in heptane with (FIG. 2B) or without (FIG. 2A) mannitol, following centrifugation, according to some embodiments of the invention (dashed lines emphasize areas with visible nanoparticle concentrations).

As shown in FIG. 2A, centrifugation of such nanoparticles resulted in a cotton ball-like precipitate, which re-dispersed immediately into the solution upon minor agitation.

Ultracentrifugation of the nanoparticles was not attempted, as it has been reported that ultracentrifugation leads to solid pellet, which may be difficult to re-disperse in the solvent [Vauthier et al., *Eur J Pharm Biopharm* 2008, 69:466-475].

Figure 2B:
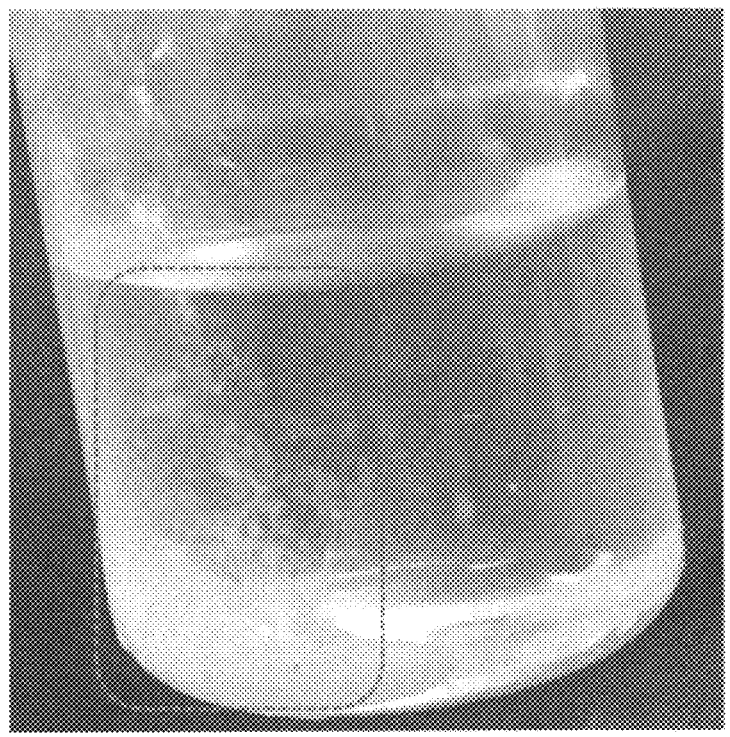

In contrast, as shown in FIG. 2B, centrifugation of the nanoparticles prepared with 240 mg/ml mannitol suspended in the anti-solvent (as described hereinabove) resulted in a pellet, which did not re-disperse upon minor agitation.

Figure 3A:
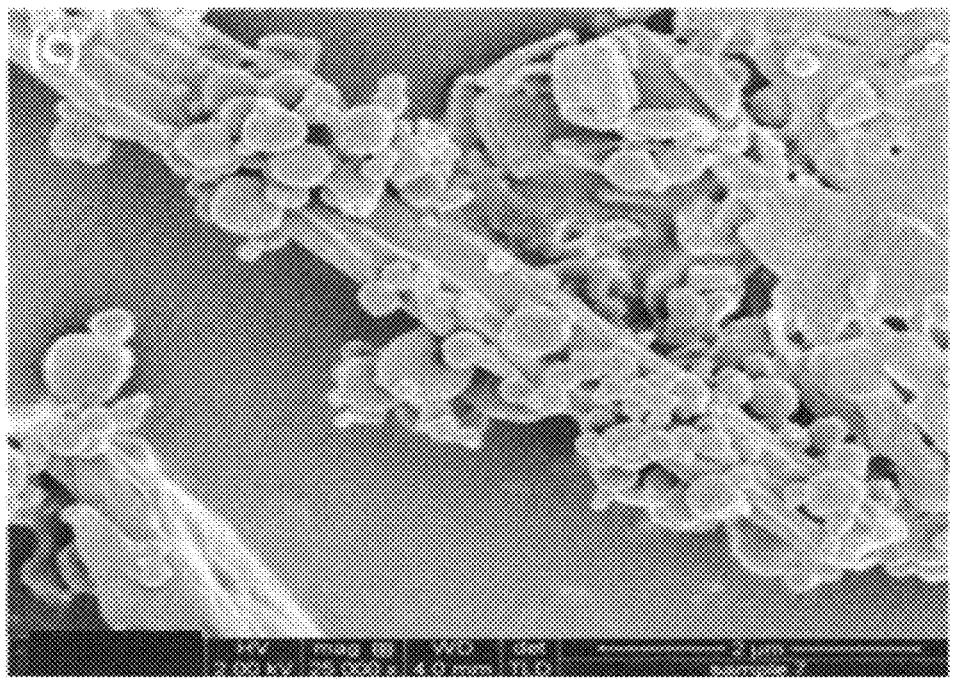
FIGS. 3A and 3B present scanning electron microscopy images of exemplary TRH-loaded PSA nanoparticles associated with surface of mannitol particles, prepared in heptane, according to some embodiments of the invention (FIG. 3A), and of mannitol particles alone (FIG. 3B).
Figure 3B:
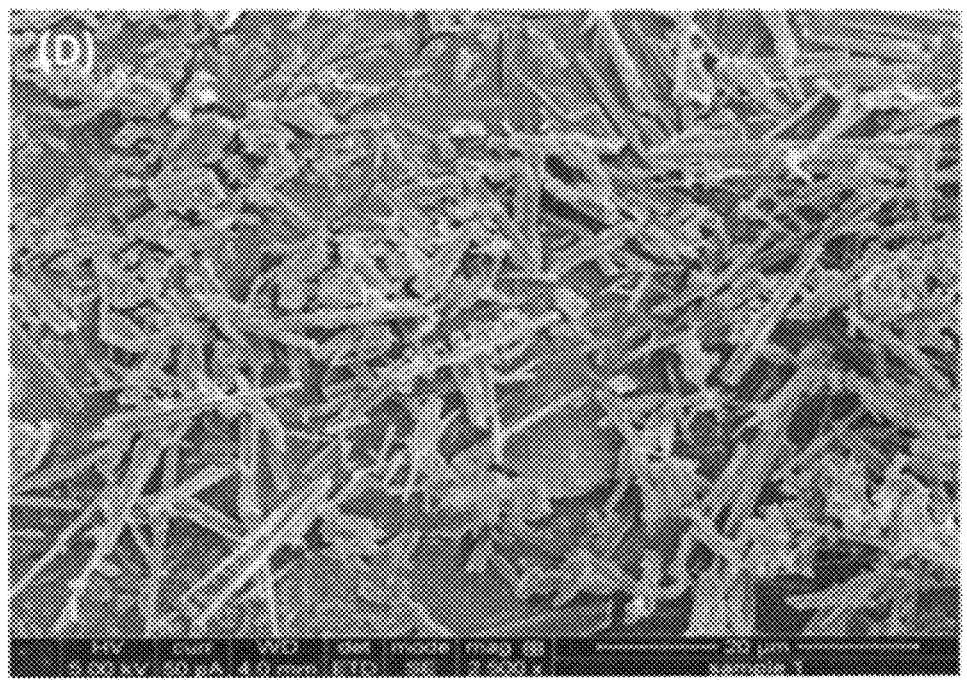

Furthermore, as shown in FIG. 3B, scanning electron microscopy showed that that mannitol is a rod-shaped molecule when suspended in heptane, which may provide adsorption sites for TRH loaded nanoparticles.

As shown in FIG. 3A, scanning electron microscopy showed that nanoparticles were adsorbed at the surface of the mannitol. This result indicates that mannitol facilitates phasing out of the nanoparticles upon centrifugation. The use of mannitol in the formulation also helps to improve the fluidization and dispersion tendencies of the NPs while adding it into water.

The drug release properties of the TRH-loaded nanoparticles were studied in vitro in either double distilled water or phosphate buffer (pH 7.2±0.2).

Figure 4:
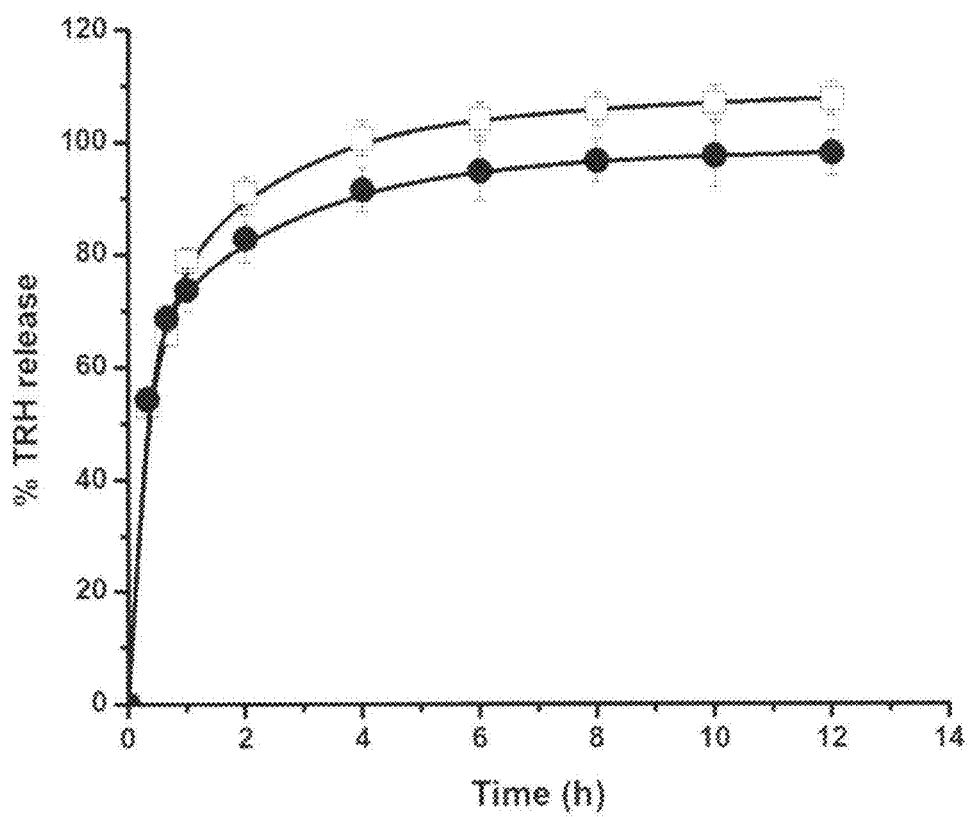
FIG. 4 is a graph showing percentage of TRH released from exemplary TRH-loaded PSA nanoparticles as a function of time, in double distilled water (full circles) and in buffer (pH 7.40) (hollow squares) at 37° C.

As shown in FIG. 4, TRH was released rapidly from TRH-loaded PSA nanoparticles upon exposure to either double distilled water or aqueous buffer (pH 7.4) at 37° C., with ~50% of the TRH being released within 30 minutes.

These results indicate that exemplary TRH-loaded PSA nanoparticles are suitable for use as a reservoir for the immediate release of the TRH into the nose and directly to the brain in cases of emergency.

As further shown therein, there was no significant difference between the release profile in water and the release profile in buffer. Buffer medium was selected for following experiments.

The degradation pathways of the TRH-loaded PSA nanoparticles in aqueous medium were studied using Fourier transform infrared (FTIR) spectroscopy.

The FTIR spectrum of exemplary PSA nanoparticles before the abovementioned release study clearly features peaks associated with the anhydride of the polymer at 1740 and 1808 cm$^{-1}$.

In comparison, the FTIR spectrum of the TRH-loaded PSA nanoparticles after the abovementioned release study features a decrease in the anhydride peak intensity at 1808 cm$^{1}$, and peaks associated with carboxylic acid appear at 1698 cm$^{-1}$ and 3500 cm$^{-1}$.

These results indicate that the anhydride polymer undergoes hydrolytic degradation in water, and that this degradation is not impeded by the presence of TRH in the polymer core. This phenomenon is important for nasal delivery, as the polymer is intended to undergo rapid hydrolysis, allowing for an immediate dose of TRH to be available during emergency medical issues.

In order to assess the stability of the TRH-loaded PSA nanoparticles, samples were stored for 6 months under three different temperature conditions, frozen (−20° C.), refrigerated (2-8° C.), and room temperature (25° C.) conditions. 100 mg of nanoparticles were stored in closed glass vials under a nitrogen atmosphere for a stability study under the specified conditions. Sampling times were 0, 1, 3 and 6 months. At these specified intervals the samples were withdrawn and checked for their physical appearance and drug content. An in vitro release test was also conducted in DDW at 37° C. (according to procedures described in the Materials and Methods section) with continuous shaking (50 rotations per minute) and without replacing the release medium. All experiments were done in triplicate.

As shown in Table 5, the TRH content of the nanoparticles did not change significantly following storage for 6 months under any of the tested temperature conditions.

TABLE 5

TRH content (% of amount of TRH used in preparation) in exemplary PSA nanoparticles before and after storage under different conditions.

| | % TRH in nanoparticles | | | |
| --- | --- | --- | --- | --- |
| Storage condition | Before storage | 1 month storage | 3 month storage | 6 month storage |
| Frozen (−20° C.) | | 99.80 | 102.68 | 103.68 |
| Refrigerated (2-8° C.) | 107.75 | 108.81 | 105.36 | 112.51 |
| Room Temperature (25° C.) | | 117.37 | 98.87 | 108.68 |

In addition, there were no observed changes in physical appearance (or color) in the samples following storage for 6 months under any of the tested temperature conditions.

These results indicate a high degree of stability of the nanoparticles under storage, including at room temperature.

Figure 5A:
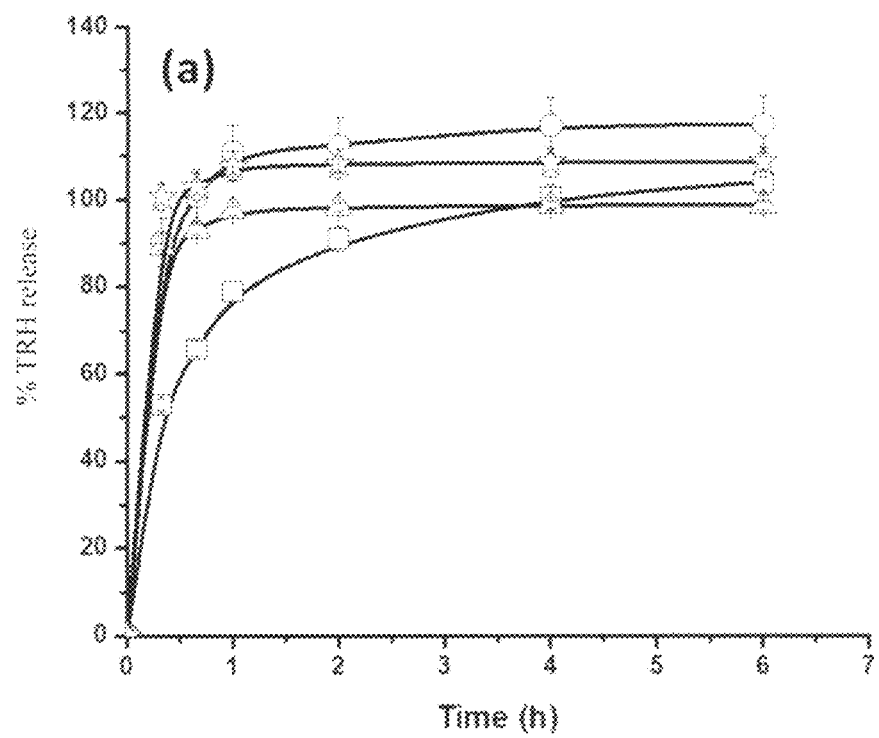
FIGS. 5A-5C are graphs showing percentage of TRH released from exemplary TRH-loaded PSA nanoparticles as a function of time, following storage at 25° C.
Figure 5B:
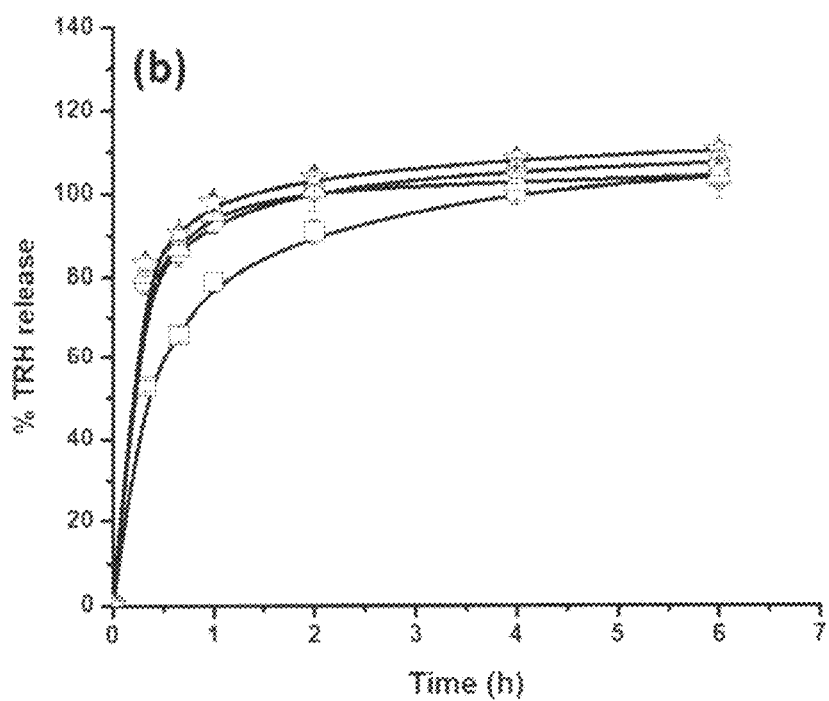
Figure 5C:
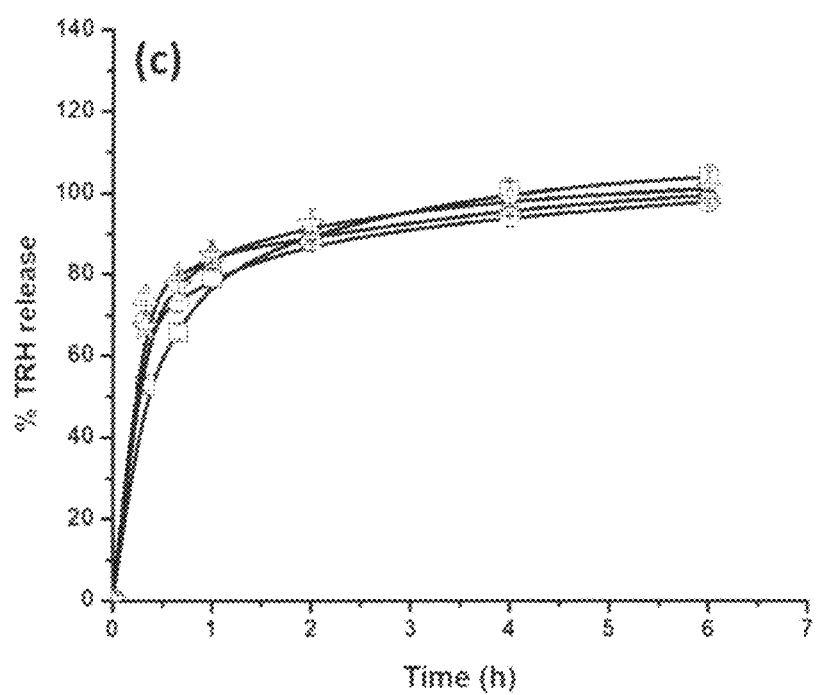

As shown in FIG. 5C, the TRH release profiles of nanoparticle samples stored at −20° C. for 1, 3 or 6 months closely resembled the initial TRH release profile.

In contrast, as shown in FIGS. 5A and 5B, the TRH release profiles of nanoparticle samples stored at ambient (25° C.; FIG. 5A) or refrigerated (2-8° C.; FIG. 5B) conditions for 1, 3 or 6 months differed significantly from the initial release profile, except that near maximal release was achieved in all cases after about two hours.

As further shown in FIGS. 5A and 5B, about 80% of the drug is released within 30 minutes, after storage for 6 months at ambient or refrigerated conditions; which suggests nanoparticle instability upon storage under such conditions.

Taken together, the above results indicate that the nanoparticles are most stable when stored under frozen conditions, which may be due to the reduced rate of degradation of the PSA under such conditions.

Example 8

Scaled Up Preparation of Thyrotropin-Releasing Hormone-Loaded Polysebacic Acid Nanoparticles After the laboratory scale preparations of nanoparticles described hereinabove, a scale up batch of TRH-loaded PSA nanoparticles was prepared.

The obtained product was a white powder (TRH content determined as 102.6%) with a PSA molecular weight of 2277 Da, and the average particle size was ~324 nm. The results of in process and finished product quality control tests performed for the batch, and their stabilities after 18 month storage at refrigerated (2-8° C.) or frozen conditions (−20° C.), are presented in Table 6.

These results reveal a close relationship between laboratory scale and industrial-scale preparation of exemplary drug-loaded nanoparticles, as well as the reliability and efficiency of the methodology described herein.

During the entire storage period of 18 months, no change was observed in physical appearance (or color) of TRH-loaded PSA nanoparticles under either refrigerated or frozen conditions.

As shown in Table 6, the determined TRH content was 91.8% and 113.1% under refrigerated conditions (2-8° C.) and between 85.1% and 106.4% under frozen conditions (−20° C.) following 18 months storage; and nanoparticle average size was increased upon storage (at all tested time points) relative to the initial size (324 nm).

Figure 6A:
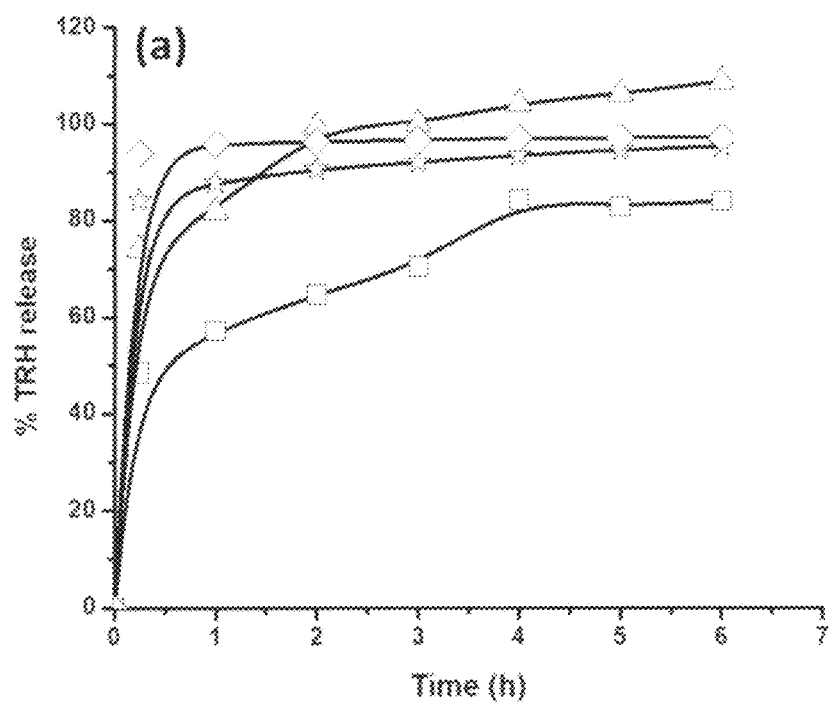
FIGS. 6A and 6B are graphs showing percentage of TRH released from exemplary TRH-loaded PSA nanoparticles (prepared as a scaled up batch) as a function of time, following storage at 2-8° C.

As further shown in FIG. 6A, the TRH release profiles of all tested nanoparticle samples stored under refrigerated conditions (2-8° C.) (for 3, 6 or 18 months) differed significantly from the initial TRH release profile, with maximal release being achieved within 1 hour.

Figure 6B:
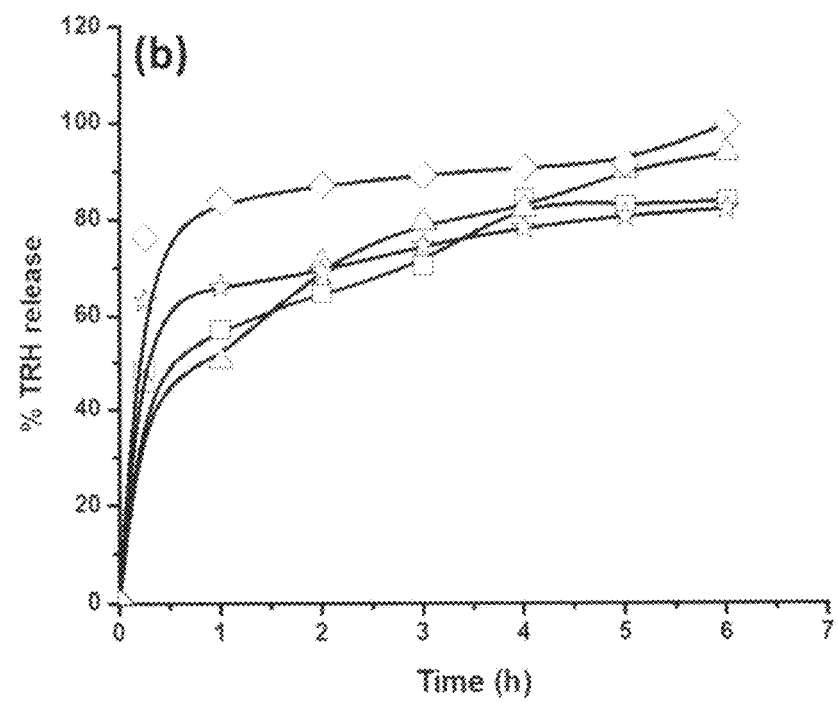

In contrast, as shown in FIG. 6B, the TRH release profiles of nanoparticle samples stored at −20° C. for 3 or 6 months are more similar to the initial TRH release profile than to TRH release profiles of samples stored under refrigerated (2-8° C.) conditions; whereas after 18 months of storage at −20° C., the TRH release profile differs significantly from the initial release profile, except that in both cases TRH release is about 80% after 4 hours.

These results indicate that the rapid release of TRH in samples stored under refrigerated conditions is due to hydrolysis of the PSA, which is largely avoided when stored at −20° C.

Example 9

Effect of TRH-Loaded Nanoparticles on Cells

A resazurin assay was utilized to determine the effect of TRH-loaded PSA nanoparticles (prepared as described in Example 7) on viability of A431 human epithelial squamous carcinoma cells, according to procedures described hereinabove.

Moderate amounts of nanoparticles did not reduce cell viability even after 3 days, suggesting that there is no significant long-term toxicity of nanoparticles.

In order to examine interaction between the nanoparticles and the cell surface, TRH-loaded PSA nanoparticles were prepared which were also loaded with indocyanine green (ICG).

ICG is an FDA-approved molecule [Alander et al., *Int J Biomed Imag* 2012, 2012:1-26] that strongly absorbs in the near-infrared spectral region, leading to strong IR fluorescence emission [Schönbächler et al., *J Photochem Photobiol A Chem* 2013, 261:12-19].

The TRH/ICG-loaded nanoparticles were prepared as described hereinabove for TRH-loaded nanoparticles. The size range of the obtained TRH/ICG-loaded PSA nanoparticles, as determined by dynamic light scattering, was 200-400 nm. This may be due to the presence of ICG, which has a large molecular weight (774.96 Da) compared to TRH (362.38 Da).

TABLE 6

Initial properties and properties following storage of exemplary scaled up nanoparticle batch

| Conditions → | Initial | | Refrigerated Conditions (2-8° C.) | | | Frozen Conditions (−20° C.) | | |
|---|---|---|---|---|---|---|---|---|
| Test ↓ | In Process | Final Product | 3 month | 6 month | 18 month | 3 month | 6 month | 18 month |
| Appearance | — | White Powder | White Powder | | | White Powder | | |
| TRH content (%) | 99.1 | 102.6 | 91.8 | 95.8 | 113.1 | 91.4 | 85.1 | 106.4 |
| Polymer molecular weight | 2671 | 2277 | 2227 | 3084 | 1372 | 3148 | 6135 | 2263 |
| Polymer polydispersity index | 2.3 | 2.0 | 1.2 | 1.2 | 1.1 | 1.4 | 1.5 | 1.2 |
| Particle size (nm) | — | 324 | 700 | 505 | 682 | 766 | 824 | 765 |
| Bacterial endotoxins | — | Pass | Pass | Pass | Pass | Pass | Pass | Pass |

Pass = <0.96 endotoxin units/vial

As determined by zeta-potential measurements, both blank PSA nanoparticles and TRH/ICG-loaded PSA nanoparticles were negatively charged, with a zeta potential of −54.7±6.27 mV and −36.8±6.19 mV, respectively.

10,000 A431 human epithelial squamous carcinoma cells were shown in each well of 96-well plates. One day after seeding the cells, every three wells were incubated with different concentrations of ICG loaded NPs for about an hour and thereafter analyzed to obtain a near infrared (NIR) image.

Figure 7A:
FIGS. 7A and 7B present an image (FIG. 7A) and a bar graph (FIG. 7B) showing near infrared (NIR) fluorescence of A431 cells incubated for 1 hour at 37° C. with 0, 0.001, 0.01, 0.1, 1, 5, 10 or 40 μg of exemplary indocyanine green (ICG)-loaded TRH-PSA nanoparticles.
Figure 7B:
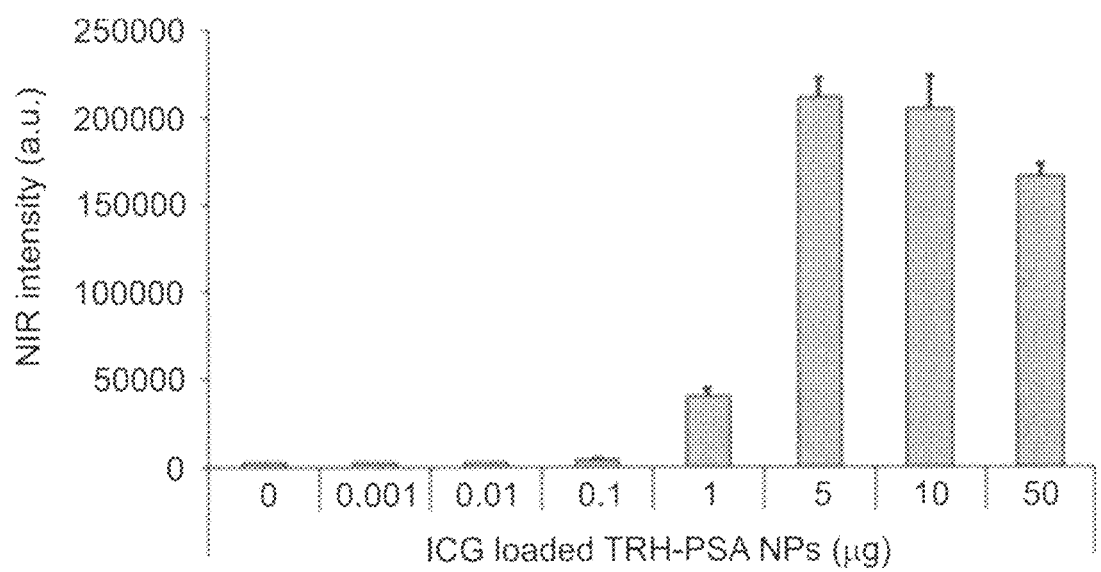

As shown in FIGS. 7A and 7B, A431 cells incubated for 1 hour at 37° C. with various amounts of TRH/ICG-loaded PSA nanoparticles exhibited fluorescence in a clear dose-dependent manner, observed both as a fluorescent image (FIG. 7A) and by quantitative near infrared spectroscopy (FIG. 7B), indicating that the nanoparticles were on the cell surface.

As further shown therein, the nanoparticles are uniformly adsorbed or attached to the surface of the cells, which is likely to facilitate transfer of loaded drugs to cells.

Taken together, the results indicate that nanoparticles prepared as described herein are suitable for effective delivery of drugs to cells.

Example 10

Preparation of Polysebacic Acid Nanoparticles by Nanoprecipitation with Surfactant-Containing Heptane Anti-Solvent and Mannitol To prepare blank nanoparticles (without a drug), 60 mg of polysebacic acid (PSA) was dissolved in 2.85 ml dichloromethane (DCM) at room temperature. The polymer solution was loaded into a syringe with a 30 G needle and injected into heptane (serving as anti-solvent) which already contained 960 mg of lyophilized mannitol (~1 micron in size) fluidized by sonication, as well as 1 mg/ml Span® 80 surfactant, at an anti-solvent to solvent ratio of 100:1. Injection of the polymer solution was over the course of three minutes while stirring (with the needle dipped inside the anti-solvent), and then stirring continued for an additional 2 minutes. The obtained particles (PSA nanoparticles and mannitol particles) were removed from the anti-solvent by centrifugation for 20 minutes at 6,000 rotations per minute, and then dried under vacuum in a desiccator. The average size of the obtained nanoparticles was 220 nm, and their polydispersity index (PDI) was 0.189.

To prepare nanoparticles loaded with thyrotropin-releasing hormone (TRH), 54 mg of polysebacic acid (PSA) was dissolved in 2.85 ml dichloromethane (DCM) at room temperature. 6 mg of TRH was dissolved in 0.5 ml ethanol and then mixed with the polymer solution. The polymer/TRH solution was loaded into a syringe with a 30 G needle and injected into heptane (serving as anti-solvent) which already contained 960 mg of lyophilized mannitol (~1 micron in size) fluidized by sonication, as well as 1 mg/ml Span® 80 surfactant, at an anti-solvent to solvent ratio of 100:1. Injection of the polymer/TRH solution was over the course of three minutes while stirring (with the needle dipped inside the anti-solvent), and then stirring continued for an additional 2 minutes. The obtained particles (TRH-loaded PSA nanoparticles and mannitol particles) were removed from the anti-solvent by centrifugation for 20 minutes at 6,000 rotations per minute, and then dried under vacuum in a desiccator. The average size of the obtained nanoparticles was ~250 nm, and their polydispersity index (PDI) was 0.204. The drug entrapment and overall yield were both above 90%.

Upon placement of the TRH-loaded nanoparticles in phosphate buffer (pH 7.4) at 37° C., the oxytocin was constantly released for over 12 hours, as determined by HPLC.

Nanoparticles containing luteinizing hormone-releasing hormone (LHRH) were prepared using essentially the same procedures as described hereinabove with respect to TRH, except that 6 mg LHRH was dissolved in 0.75 ml acetic acid and 0.6 ml ethanol. The average size of the obtained nanoparticles was ~300 nm, and their polydispersity index (PDI) was 0.3.

Nanoparticles containing oxytocin were prepared using essentially the same procedures as described hereinabove with respect to TRH, except that 6 mg oxytocin was dissolved in 0.75 ml acetic acid and 0.5 ml ethanol. The average size of the obtained nanoparticles was ~200 nm, and their polydispersity index (PDI) was 0.287. The drug entrapment and overall yield were both above 70%.

Upon placement of the oxytocin-loaded nanoparticles in phosphate buffer (pH 7.4) at 37° C., the oxytocin was constantly released for over 6 hours, as determined by HPLC.

These results indicate that the process of preparation of nanoparticles is also suitable for peptides larger than TRH.

Example 11

Preparation of Poly(D,L-Lactide-Co-Glycolide) Nanoparticles by Nanoprecipitation with Heptane Anti-Solvent and Mannitol A variety of nanoparticles, with and without a loaded drug, were prepared from different types of PLGA (poly(D, L-lactide-co-glycolide) by nanoprecipitation using heptane as an anti-solvent.

To prepare blank nanoparticles (without a drug), 60 mg of PLGA (poly(D,L-lactide-co-glycolide) with a 1:1 molar ratio of lactide to glycolide was dissolved in 1 ml dichloromethane at room temperature. The polymer solution was loaded into a syringe with a 30 G needle and injected into heptane (serving as anti-solvent) which already contained 960 mg of lyophilized mannitol (~1 micron in size) fluidized by sonication, as well as 1 mg/ml Span® 80 surfactant, at an anti-solvent to solvent ratio of 100:1. Injection of the polymer solution was over the course of three minutes while stirring (with the needle dipped inside the anti-solvent), and then stirring continued for an additional 2 minutes. The obtained particles (PLGA nanoparticles and mannitol particles) were removed from the anti-solvent by centrifugation for 20 minutes at 6,000 rotations per minute, and then dried under vacuum in a desiccator. The average size of the obtained nanoparticles was 247 nm, and their polydispersity index (PDI) was 0.431.

In an alternative process, blank nanoparticles were prepared by essentially the same procedures as described hereinabove, except that 60 mg of PLGA (poly(D,L-lactide-co-glycolide) with a 3:1 molar ratio of lactide to glycolide was dissolved in 2.85 ml dichloromethane. The average size of the obtained nanoparticles was 248 nm, and their polydispersity index (PDI) was 0.215.

To prepare nanoparticles loaded with thyrotropin-releasing hormone (TRH), 54 mg of the abovementioned PLGA was dissolved in 1 ml dichloromethane at room temperature. 6 mg of TRH was dissolved in 0.5 ml ethanol and then mixed with the polymer solution. The polymer/TRH solution was loaded into a syringe with a 30 G needle and injected into heptane (serving as anti-solvent) which already contained 960 mg of lyophilized mannitol (~1 micron in size) fluidized by sonication, as well as 1 mg/ml Span® 80 surfactant, at an anti-solvent to solvent ratio of 100:1. Injection of the polymer/LHRH solution was over the course of three minutes while stirring (with the needle dipped inside the anti-solvent), and then stirring continued for an additional 2 minutes. The obtained particles (TRH-loaded PSA nanoparticles and mannitol particles) were removed from the anti-solvent by centrifugation for 20 minutes at 6,000 rotations per minute, and then dried under vacuum in a desiccator. The average size of the obtained nanoparticles was ~250 nm, and their polydispersity index (PDI) was 0.35.

In an alternative process, TRH-loaded nanoparticles were prepared by essentially the same procedures as described hereinabove, except that 60 mg of PLGA (poly(D,L-lactide-co-glycolide) with a 3:1 ratio of lactide to glycolide was dissolved in 2.85 ml dichloromethane. The obtained particles (TRH-loaded PSA nanoparticles and mannitol particles) were removed from the anti-solvent by centrifugation for 15 minutes at 6,000 rotations per minute, and then dried under vacuum in a desiccator. The average size of the obtained nanoparticles was ~280 nm, and their polydispersity index (PDI) was 0.369.

Upon placement of the TRH-loaded nanoparticles (prepared by either of the abovementioned protocols) in phosphate buffer (pH 7.4) at 37° C., the TRH was constantly released for over 12 hours, as determined by HPLC.

Nanoparticles containing oxytocin were prepared using essentially the same procedures as described hereinabove with respect to TRH, except that the 54 mg PLGA (with a 1:1 or 3:1 molar ratio of lactide to glycolide) was dissolved in 2.85 ml of dichloromethane, and 6 mg oxytocin was dissolved in 0.75 ml acetic acid and 0.5 ml ethanol. The average size of the nanoparticles obtained using 1:1 PLGA was ~200 nm, and their polydispersity index (PDI) was 0.280. The average size of the nanoparticles obtained using 3:1 PLGA was ~300 nm, and their polydispersity index (PDI) was 0.291.

Upon placement of the oxytocin-loaded nanoparticles (prepared by either of the abovementioned protocols) in phosphate buffer (pH 7.4) at 37° C., the oxytocin was constantly released for over 6 hours, as determined by HPLC.

Nanoparticles containing luteinizing hormone-releasing hormone (LHRH) and PLGA with a 1:1 or 3:1 molar ratio of lactide to glycolide were prepared using essentially the same procedures as described hereinabove with respect to oxytocin, except that 6 mg LHRH was dissolved in 0.75 ml acetic acid and 0.6 ml ethanol. The average size of the nanoparticles obtained using 1:1 PLGA was ~200 nm, and their polydispersity index (PDI) was 0.310. The average size of the nanoparticles obtained using 3:1 PLGA was ~300 nm.

These results indicate nanoprecipitation according to procedures described herein can be used to prepare a wide variety of nanoparticles from different polymers and different loaded drugs.

Example 12

Effects of Different Parameters on Nanoparticle Preparation by Nanoprecipitation Without being bound by any particular theory, the basic principle of the nanoprecipitation technique is believed to be interfacial precipitation of a polymer after adding the polymer solution to an anti-solvent, wherein the polymer precipitates in the form of nanoparticles due to the fall in interfacial tension.

A suitable solvent system must solubilize the drug and polymer in a single solvent system, while being miscible with the anti-solvent.

The following solvents were compared for use as drug solvents in nanoprecipitation: acetone, ethanol, tetrahydrofuran (THF), acetic acid, acetonitrile, dimethylsulfoxide (DMSO), dimethylformamide (DMF), N-methylpyrrolidone (NMP), methanol, n-propanol and isopropanol.

Chloroform, dichloromethane (DCM), ethanol, acetone, methanol and ethyl acetate were tested as polymer solvents.

Drugs (thyrotropin-releasing hormone (TRH), oxytocin, and luteinizing hormone-releasing hormone (LHRH)) and polymers (polysebacic acid, and PLGA (poly(lactide-co-glycolide)) with either a 1:1 or 3:1 molar ratio of lactide to glycolide) were added to 1 ml of test solvent and stirred vigorously by vortex.

Ethanol was found to be the best solvent for dissolving TRH, and acetic acid was found to be the best solvent for oxytocin and LHRH. These solvents required the smallest amount of solvent for immediate solubilization of the drug.

DCM was found to be the best solvent for polysebacic acid, and ethyl acetate was found to be the best solvent for PLGA. These solvents are miscible with the solvents used to solubilize the drugs, and mixing the drug solution and polymer solution resulted in a clear and stable solution.

Various volatile, relatively non-toxic organic solvents (heptane, hexane, pentane, diethyl ether, toluene and ethyl acetate) were then tested for their suitability as an anti-solvent in nanoprecipitation. The relevant criteria for an anti-solvent are miscibility with the drug-polymer solvent system, and formation of nanoparticles in which the obtained mean size and polydispersity index (PDI) are both relatively low. A 100:1 anti-solvent to solvent ratio was used consistently during these tests.

Heptane was found to provide the best results (particle sizes of 200-300 nm and a PDI of ~0.3), followed by hexane and pentane.

The effects of a surfactant on nanoprecipitation were then assessed by comparing the effect of a surfactant (0.2 mg/ml Span® 80 surfactant) added to a solvent (DCM) to the effect of the same surfactant added to an anti-solvent (heptane).

Surfactant added to the anti-solvent was found to provide superior results, with smaller particle size (200-250 nm) and PDI (0.2-0.4).

The effect of surfactant concentration was then assessed, using 0.21, 0.5, 1, 1.5, 2, 2.5 or 5 mg/ml of Span® 80 surfactant, usually added to the heptane anti-solvent. Blank nanoparticles were formed from polysebacic acid according to procedures described in Example 10, except that the surfactant concentration was varied.

TABLE 7

Particles size results of polysebacic acid nanoparticles prepared with different surfactant concentrations

| Span ® 80 concentration (mg/ml) | Phase with Span ® 80 | Average particle size (nm) | Polydispersity index (PDI) |
|---|---|---|---|
| 0.21 | internal phase (DCM) | 1394 | 0.748 |
| 0.21 | external phase | 284.8 | 0.314 |
| 0.5 |  | 295.3 | 0.248 |

TABLE 7-continued

Particles size results of polysebacic acid nanoparticles prepared with different surfactant concentrations

| Span® 80 concentration (mg/ml) | Phase with Span® 80 | Average particle size (nm) | Polydispersity index (PDI) |
|---|---|---|---|
| 1 | (heptane) | 152.6 | 0.227 |
| 1.5 | | 148.1 | 0.314 |
| 2.5 | | 317.6 | 0.593 |
| 5 | | 356.9 | 0.418 |

As shown in Table 7, the smallest nanoparticles were obtained with 1 or 1.5 mg/ml surfactant in the heptane anti-solvent, and the lowest polydispersity was obtained with 1 mg/ml surfactant.

These results indicate that an optimal concentration of Span® 80 surfactant is about 1 mg/ml.

The effect of different aqueous dispersion media on the nanoparticles was investigated, as it is desirable to minimize aggregation and sedimentation of nanoparticles upon re-dispersion of the dry nanoparticle composition.

Double distilled water (DDW) and solutions of 1 mg/ml Tween® 80 or Tween® 20 surfactant in DDW were compared. 5 mg of nanoparticle powder was placed in a glass vial and 20 ml of aqueous medium was added and then mixed by vortex for 5 minutes. Re-dispersion was assessed visually.

A clear suspension was obtained with DDW, whereas visible particle aggregation and sedimentation was present in samples with the surfactants. Additional sonication (2-10 minutes) did not appear to further disperse the agglomerates.

These results indicate that water is a highly suitable solvent for re-dispersion of the nanoparticles.

The effect of various water-soluble compounds (e.g., other than mannitol) on re-dispersion were also compared. Blank PSA nanoparticles were prepared according to procedures described in Example 10, except that in some samples, sucrose, dextrose or trehalose was used instead of mannitol, and various concentrations of the aforementioned sugars (4, 8, 12, 16 or 20 mg per 1 mg of polymer) were compared. 5 mg of dry nanoparticles were placed in a glass vial and 20 ml of DDW was added and then mixed by vortex for 5 minutes. Re-dispersion was assessed visually.

Samples with mannitol resulted in a more uniform appearance upon re-dispersion than did samples with sucrose, dextrose or trehalose. In addition, 16 mg mannitol per 1 mg of polymer provided the best results.

These results indicate that mannitol is a particularly suitable water-soluble compound for inclusion in a nanoparticle composition.

In view of the above, further experiments used the following procedures: 54 mg of PSA was dissolved in 2.85 ml dichloromethane. 6 mg of the drug TRH was dissolved in 0.5 ml ethanol and mixed with the polymer solution. The drug/polymer solution was loaded in to a syringe with 30 G needle and injected into cold heptane (8-10° C., in a bottle surrounded with ice) containing Span® 80 surfactant (1 mg/ml), with anti-solvent to solvent weight ratio of 100:1. The anti-solvent was stirred continuously using magnetic stirrer. The needle was dipped inside the anti-solvent while adding drug/polymer solution and the injection was over the course of three minutes. After complete addition of drug/polymer solution, stirring was continued for additional two minutes and the batch was analyzed for particle size. In addition, 240 mg of lyophilized mannitol were suspended in 50 ml heptane and sonicate for 20 minutes. The lyophilized mannitol was then added to heptane used to prepare nanoparticles. The nanoparticles and mannitol particles were removed from the anti-solvent by centrifugation for 20 minutes at 6,000 rotations per minute and then dried under a vacuum in a desiccator. The final product kept in a sealed vial under dry atmosphere and in a freezer at −20° C.

Example 13

Toxicity Study of Intranasal Administration of Drug-Loaded Nanoparticles in Monkeys In order to assess the possible toxicity of exemplary TRH-loaded PSA nanoparticles formulated for intranasal administration, a test article was administered two times daily intranasally to cynomolgus monkeys for at least 28 days. The reversibility, persistence, or delayed occurrence of any effects after at least a 14 day recovery phase were assessed.

Male and female cynomolgus monkeys (*Macaca fascicularis*) of Asian origin were assigned to five groups, and doses were administered as indicated in Table 8. Groups 1 through 5 were dosed intranasally twice daily (approximately 3 hours apart, based on the last animal dosed/sex/group from the first daily dose) for at least 28 days at a volume of 50 μl/spray to one (Group 3 only) or both (Groups 1, 2, 4, and 5) nostrils. Group 5 was administered fluoxetine via oral gavage once daily beginning 7 days prior to administration of TRH-loaded PSA nanoparticles at a dose volume of 0.5 ml/kg. The vehicle control article was polysebacic acid (PSA), and the saline control was 0.9% sodium chloride for injection, USP (sterile saline).

Assessment of toxicity was based on mortality, clinical observations, body weights, body weight change, qualitative food consumption, ophthalmic observations, electrocardiographic (ECG) measurements, and clinical and anatomic pathology.

No PSA or TRH-PSA related mortality occurred. All animals survived until their scheduled sacrifice interval. No differences in clinical observations; body weights; qualitative food consumption; ophthalmic observations; ECG changes; hematology, coagulation, or urinalysis tests; organ weights; or macroscopic findings were attributed to TRH-PSA or fluoxetine+TRH-PSA.

TABLE 8:

Protocol of toxicity study in monkeys

| Group | No. of Animals | | Dose Level (μgTRH/ dose) | Dose Level (μgTRH/ day) | Dose Concentration (μg TRH/mL) |
|---|---|---|---|---|---|
| | Male | Female | | | |
| 1 (Vehicle Control Article)[a, b, c] | 5 | 5 | 0 | 0 | 0 |

TABLE 8:-continued

Protocol of toxicity study in monkeys

| Group | No. of Animals | | Dose Level | | Dose Concentration |
|---|---|---|---|---|---|
| | Male | Female | (µgTRH/ dose) | (µgTRH/ day) | (µg TRH/mL) |
| 2 (Saline Control)[b, d] | 3 | 3 | 0 | 0 | 0 |
| 3 (Low)[e] | 3 | 3 | 80 | 160 | 1600 |
| 4 (High)[a, b] | 5 | 5 | 320 | 640 | 3200 |
| 5 (fluoxetine + High)[b, f] | 3 | 3 | 320 | 640 | 3200 |

[a] Animals designated for recovery sacrifice (two animals/sex in Groups 1 and 4) underwent at least 2 weeks of recovery following the dosing phase.
[b] Groups 1, 2, 4, and 5 were administered (50 µL/spray) in both nostrils twice/day approximately 3 hours apart based on the last animal dosed/sex/group.
[c] Group 1 was administered vehicle control article at 2.9 mg/dose (5.8 mg/day). The powder in each vial of placebo and test article contained 18% PSA. When reconstituted with 0.5 mL reverse osmosis (RO) water, the resultant PSA concentration was 29 mg/mL.
[d] Group 2 was administered saline (50 µL/spray).
[e] Group 3 was administered (50 µL/spray) in the left nostril once/day and then in the right nostril approximately 3 hours later based on the last animal dosed/sex/group.
[f] Group 5 was administered 2 mg/kg fluoxetine at a dose volume of 0.5 mL/kg by oral gavage once daily beginning 7 days before administration of TRH-PSA, and continued through the dosing phase.

On Day 15 of the dosing phase, minimally to mildly increased T3 concentration was noted in all males administered fluoxetine+640 µg TRH/day and most to all females administered 160 or 640 µg TRH/day or fluoxetine+640 µg TRH/day. Minimally to mildly increased T4 concentration was also observed on Day 15 of the dosing phase in most to all animals administered 640 µg TRH/day or fluoxetine+640 µg TRH/day and in males administered 160 µg TRH/day. Changes in T3 and T4 concentrations were not observed on Day 29 of the dosing phase or Day 15 of the recovery phase and had no specific microscopic correlates.

Congestion of the nasal turbinates in animals administered 160 or 640 µg TRH/day or fluoxetine+640 µg TRH/day was the most pronounced microscopic finding at the terminal and recovery sacrifices. The addition of fluoxetine (Group 5) did not appreciably alter findings. Other findings in the nasal tissues at the terminal sacrifice, consisting of cellular infiltrates (mononuclear cell and mixed cell population), edema, metaplasia, hyperplasia, and erosion/ulceration, generally had reduced incidences and/or severities at the recovery sacrifice.

In conclusion, no adverse systemic effects were found following intranasal administration of 5.8 mg/day PSA or up to 640 µg TRH/day TRH-PSA to cynomolgus monkeys for 28 days. Additionally, intranasal administration of 640 µg TRH/day in combination with oral gavage administration of 2 mg/kg/day fluoxetine was similarly well-tolerated. Administration of 160 or 640 µg TRH/day produced the moderately severe, adverse microscopic changes local to nasal application sites. These consisted most commonly of congestion, which affected approximately 22% of animals, and, less commonly, erosion/ulceration, which affected approximately 8% of animals. Although viewed as adverse local changes in the monkey, they did not manifest themselves in a clinically apparent manner.

Example 14

Cardiovascular Effects of Intranasal Administration of Drug-Loaded Nanoparticles In order to assess the possible cardiovascular effects of exemplary TRH-loaded PSA nanoparticles formulated for intranasal administration, a test article was administered as a single dose intranasally to instrumented naive male cynomolgus monkeys in a Latin square dosing design.

Four naive male cynomolgus monkeys were administered a single intranasal dose of saline control (0.9% sodium chloride for injection, USP (sterile saline)), vehicle control article (polysebacic acid (PSA)), or TRH-PSA at a dose of 640 µg TRH, with or without 2 mg/kg fluoxetine pretreatment in a Latin square dosing design. Dose formulations, except fluoxetine, were administered intranasally using a Precision Olfactory Delivery (POD) nasal device at a volume of 200 µl/animal/dose (50 µl/spray×2 to each nostril). Fluoxetine was administered via oral gavage at a dose volume of 0.5 ml/kg, 2 to 2.5 hours prior to administration of TRH-PSA.

Assessment of cardiovascular function was based on qualitative electrocardiogram (ECG) evaluation and quantitative analysis of ECG parameters (PR interval, QRS duration, QT interval, and corrected QT [QTc] interval) and hemodynamic parameters (heart rate; systolic, diastolic, and mean arterial pressures; arterial pulse pressure). Telemetry ECG, arterial blood pressure, and body temperature data were recorded for at least 90 minutes prior to intranasal dosing and continuously through at least 19 hours post-dose on Days 1, 8, 15, and 22 of the dosing phase. Assessment of general health was based on mortality, clinical observations, and body weights.

All animals survived until their scheduled transfer back to the stock colony on Day 23 of the dosing phase. No abnormal clinical observation or change in body weight was attributed to intranasal administration of TRH-PSA (with or without fluoxetine pretreatment) or PSA.

No qualitative ECG effect or change in PR interval, QRS duration, QT interval, QTc interval, heart rate, arterial pressures, or body temperature was attributed to intranasal administration of TRH-PSA (with or without fluoxetine pretreatment) or PSA.

In conclusion, cardiovascular function was assessed in four naïve male cynomolgus monkeys administered a single intranasal dose of saline control, vehicle control article, or TRH-PSA (at 640 µg TRH), with or without fluoxetine pretreatment, in a Latin square dosing design. No TRH-PSA- or PSA-related mortality, morbidity, or effects on body weight were noted. No qualitative ECG effect or quantitative change in PR interval, QRS duration, QT interval, QTc interval, heart rate, arterial pressures, or body temperature was attributed to intranasal administration of TRH-PSA (with or without fluoxetine pretreatment) or PSA.

Example 15

Toxicity Study of Intranasal Administration of Drug-Loaded Nanoparticles in Rats In order to assess the possible toxicity of exemplary TRH-loaded PSA nanoparticles formulated for intranasal administration, a test article was administered two times daily intranasally to rats for at least 42 days. The reversibility, persistence, or delayed occurrence of any effects after at least a 14 day recovery phase were assessed.

Male and female rats were assigned to four groups, and doses were administered as indicated in Table 9. Animals were dosed intranasally twice daily (approximately 3 hours apart) for 42 days at a volume of 10 µl/dose. The vehicle control article was polysebacic acid (PSA), and the saline control was 0.9% sodium chloride for injection, USP (sterile saline). Due to a technical error, an incorrect and lower dose volume was administered on Days 1 through 15 of the dosing phase, resulting in administration of a lower dose on these days (approximately 52% of the target dose).

TABLE 9

Protocol of toxicity study in rats

| Group | No. of Animals | | Dose Level (μgTRH/ dose) | Dose Level (μgTRH/ day) | Dose Concentration (μg TRH/mL) |
|---|---|---|---|---|---|
| | Male | Female | | | |
| 1 (Vehicle Control Article)[a, b] | 15 | 15 | 0 | 0 | 0 |
| 2 (Saline Control)[a, c] | 15 | 15 | 0 | 0 | 0 |
| 3 (Low)[d] | 10 | 10 | 16 | 32 | 1600 |
| 4 (High)[a, e] | 15 | 15 | 64 | 128 | 3200 |

[a]Animals designated for recovery sacrifice (five animals/sex/group in Groups 1, 2, and 4) underwent 2 weeks of recovery following the dosing phase.
[b]Group 1 was administered vehicle control article at 2.9 mg/dose (5.8 mg/day). The powder in each vial of placebo and test article contained 18% PSA. When reconstituted with 0.5 mL RO water, the resultant PSA concentration was 29 mg/mL.
[c]Group 2 was administered saline (10 μL)
[d]Group 3 was administered 10 μL in the left nostril and then again with 10 μL in the right nostril approximately 3 hours later based on the last animal dosed/sex/group.
[e]Group 4 was administered 10 μL in each nostril and then again in each nostril approximately 3 hours later based on the last animal dosed/sex/group.

Assessment of toxicity was based on mortality, clinical observations, body weights, food consumption, ophthalmic observations, and clinical and anatomic pathology. Blood samples were collected for prolactin and thyroid hormone analyses.

All animals survived to their scheduled sacrifice. No differences in clinical observations, body weight, food consumption, or ophthalmic observations were attributed to TRH-PSA in animals administered 32 or 128 μg TRH/day.

No TRH-PSA-related change in hematology, coagulation, clinical chemistry, or urinalysis parameters or thyroid stimulating hormone (TSH) concentrations occurred in animals administered 32 or 128 μg TRH/day.

TRH-PSA-related changes in T3 and T4 concentrations were limited to females administered ≥32 μg TRH/day and exhibited differing patterns between Day 15 and Day 43 of the dosing phase, consistent with the administration of a lower dose of TRH-PSA on Days 1 to 15. On Day 15 of the dosing phase, these changes consisted of minimal increases in triiodothyronine (T3) concentrations in females administered ≥32 μg TRH/day and thyroxine (T4) concentrations in females administered 128 μg TRH/day. At the end of the dosing phase (Day 43), minimal and reversible decreases in T3 and T4 concentrations were noted in females administered 128 μg TRH/day. These minimal changes were non-adverse.

Administration of TRH-PSA intranasally resulted in no change in organ weights or any macroscopic observation during the dosing or recovery phase, nor any microscopic observations during the dosing phase.

In conclusion, intranasal administration of up to 32 or 128 μg TRH/day for 42 days was well-tolerated and without adverse effects in rats.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition, comprising:
a plurality of nanoparticles, said nanoparticles comprising a biodegradable water insoluble polymer selected from the group consisting of polysebacic (PSA), poly (1,3-bis-carboxyphenonypropane-co-sebacic acid (P(CPP-SA) and poly(D,L-lactide-co-glycolide) (PLGA); and
an agent incorporated in said polymer;
wherein said nanoparticles are associated with a surface of mannitol, wherein the nanoparticle is formed by nanoprecipitation of the biodegradable water-insoluble polymer in an anti-solvent, the anti-solvent including the mannitol;
wherein, upon contact with water, said nanoparticles in the composition disperse within two minutes.

2. The composition of claim 1, wherein an average diameter of said nanoparticles comprising a biodegradable polymer is in a range of from 10 nm to 1000 nm, optionally from 200 nm to 600 nm.

3. The composition of claim 1, wherein an average diameter of said water-soluble particles is in a range of from 500 nm to 50000 nm.

4. The composition of claim 1, wherein a weight ratio of said nanoparticle comprising a biodegradable polymer to said water-insoluble particle is in a range of from 1:2 to 1:100.

5. The composition of claim 1, wherein a concentration of said agent in said nanoparticles comprising a biodegradable lipid and/or polymer is at least 5 weight percent.

6. The composition of claim 1, wherein said agent is water soluble.

7. The composition of claim 1, wherein an average size of said mannitol is in a range of from 500 nm to 50000 nm.

8. The composition of claim 1, wherein a weight ratio of said nanoparticles comprising a polymer to the water-soluble compounds in the composition is in a range of from 1:2 to 1:100.

9. The composition of claim 1, wherein the agent is a therapeutically active agent selected from the group consisting of: thyrotropin-releasing hormone (TRH), gonadotropin-releasing hormone (LHRH), oxytocin, insulin, corticotropin (ACTH), cyclosporin, steroids, cannabidiol (CBD), tetrahydrocannabinol (THC), rapamycin, and antibiotics.

10. The composition of claim 9, wherein said nanoparticle is a polymer comprising polysebacic acid, the agent is LHRH and the water-soluble compound is mannitol, and wherein the nanoprecipitation has an overall process yield of greater than 90%.

11. The composition of claim 1, wherein the composition is suitable for nasal administration to a patient.

12. The composition according to claim 11, wherein said nasal administration is for delivering the therapeutically active agent to the brain.

13. The composition of claim 1, wherein the agent is thyrotropin-releasing hormone, and the agent is used to treat a condition selected from the group consisting of: a depressive disorder and epilepsy.

14. The composition of claim 9, wherein said nanoparticle is a polymer comprising polysebacic acid, the agent is CBD and the water-soluble compound is mannitol, and wherein the nanoprecipitation has an overall process yield of greater than 90%.

15. The composition of claim 9, wherein said nanoparticle is a polymer comprising polysebacic acid, the agent is dexamethasone and the water-soluble compound is mannitol, and wherein the nanoprecipitation has an overall process yield of greater than 90%.

16. The composition of claim 9, wherein said nanoparticle is a polymer comprising polysebacic acid, the agent is oxytocin and the water-soluble compound is mannitol, and wherein the nanoprecipitation has an overall process yield of greater than 90%.

* * * * *